United States Patent [19]

Werbel et al.

[11] Patent Number: 4,659,708

[45] Date of Patent: Apr. 21, 1987

[54] ANTI-LEISHMANIAL LEPIDINE DERIVATIVES

[75] Inventors: Leslie M. Werbel, Ann Arbor, Mich.; Edgar A. Steck, Silver Spring, Md.

[73] Assignee: The United States of America as represented by the Secretary of the Army, Washington, D.C.

[21] Appl. No.: 294,661

[22] Filed: Aug. 20, 1981

Related U.S. Application Data

[63] Continuation-in-part of Ser. No. 183,514, Sep. 2, 1980, abandoned.

[51] Int. Cl.$^4$ ............... C07D 401/00; C07D 279/12; A61K 31/435; A61K 31/54
[52] U.S. Cl. .................... 514/222; 544/58.2; 544/58.6; 544/62; 544/128; 544/360; 544/363; 514/227; 514/253
[58] Field of Search ............... 544/360, 363, 62, 58.2, 544/128; 546/171; 514/222, 227, 253

[56] References Cited

U.S. PATENT DOCUMENTS

| | | | |
|---|---|---|---|
| 2,508,937 | 5/1950 | Campbell | 546/171 |
| 3,142,679 | 7/1964 | Barrett et al. | 544/363 |
| 4,167,638 | 9/1979 | Chen et al. | 546/171 |
| 4,209,519 | 6/1980 | Kinnamon | 544/363 |

FOREIGN PATENT DOCUMENTS

| | | | |
|---|---|---|---|
| 538289 | 3/1957 | Canada | 546/171 |
| 635080 | 1/1962 | Canada | 544/363 |
| 645414 | 7/1962 | Canada | 544/128 |
| 658368 | 2/1963 | Canada | 544/363 |

OTHER PUBLICATIONS

Kinnamon, K. E., et al., Am. J. Trop. Med. Hyg. 27 (4), pp. 751-757 (1978).

*Primary Examiner*—George F. Lesmes
*Assistant Examiner*—S. A. Gibson
*Attorney, Agent, or Firm*—William G. Gapcynski; Arthur I. Spechler; Werten F. W. Bellamy

[57] ABSTRACT

The subject 8-[6-(N-heterocyclic-substituted)hexylamino]-6-methoxy lepidine derivatives have the formula:

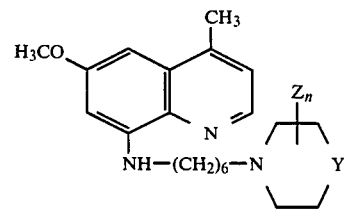

wherein Z represents methyl or, together with the two contiguous carbon atoms, the benzo moiety of a benzopiperazinyl derivative when Y is —N(R')—, n is an integer from 0 to 2; Y represents —O—, —S—, —S(O)—, —S(O)$_2$—, and —N(R')—; R' represents hydrogen, alkyl, lower alkyl, R" substituted lower alkyl, cycloalkyl, aryl, sulfonyl, saturated 1,4-diazepinyl, lower alkyl N-cyanocarboximidothioate, or —C(O)R'''; R" represents at least one of hydroxy, alkoxy, aralkoxy, amino, lower alkyl substituted amino, phenyl, halogenated phenyl, or sufonyl; and R''' represents lower alkyl, alkoxy, aralkoxy, amino, lower alkyl substituted amino or aryl substituted amino; and pharmaceutically acceptable salts thereof. These derivatives afford improvement in means for the chemotherapy of leishmaniasis when administered parenterally or orally to infected animals.

56 Claims, No Drawings

ANTI-LEISHMANIAL LEPIDINE DERIVATIVES

GOVERNMENT RIGHTS

The invention described herein may be manufactured and used by or for the Government, for governmental purposes, without the payment of any royalties thereon or therefor.

CROSS REFERENCE TO RELATED APPLICATIONS

This application is a continuation-in-part of application Ser. No. 183,514, filed Sept. 2, 1980, now abandoned.

BACKGROUND OF THE INVENTION

The invention generally relates to the chemotherapy or treatment of leishmaniasis. Leishmania are well known intra-cellular protozoan parasites which may give rise to serious infections in man. The organisms are transmitted by the "bite" of an infected sandfly, and invade the reticulo-endothelial system (RES). The parasites are highly successful in their ability to grow and multiply in the very tissues of the vertebrate host which are responsible for reaction to invading organisms. Expectedly, such location of Leishmania renders difficult a satisfactory approach to chemotherapy, and there is highly complex inter-play between parasites and cellular immune responses of the host. In the RES, the parasites lie within the host macrophage for at least part of their life cycle. Fusion of host cell secondary lysosomes with the parasitophorous vacuoles apparently occurs without preventing subsequent multiplication of the Leishmania. Such fusion may provide means for access for nutrients to the parasite, but also exposes the parasite to host antibodies and lysosomal enzymes. In man, the result of successful invasion of the spleen and liver by Leishmania donovani most frequently is death. Scarring of the skin may be the sole manifestation of infection with Leishmania tropica and allied dermatotropic organisms (as, Leishmania aethiopica, L. mexican, L. peruviana, and L. guyanensis). Intermediate in severity are invasions of muco-cutaneous tissues by Leishmania braziliensis. There are considerable differences among various animals in their response to leishmanial infections, however, a satisfactory animal model for laboratory trials has been found in Leishmania donovani infections in the gold hamster.

The L. donovani-hamster model has been used widely to assess candidate drugs for anti-leishmanial effects. Unfortunately, relatively few drugs have been found to show appreciable activity on screening, and fewer yet have merited trial in man. Antimony drugs are a mainstay for treatment despite evaluation of diverse types both in the laboratory and in clinical trials. Pentavalent compounds of antimony are better tolerated than trivalent antimonials, yet severe toxic side effects may occur, in particular, among poorly nourished patients. Toxicity of such drugs may affect the liver (hepatitis), kidneys (nephritis), or the heart (myocarditis). Of these toxic effects, myocarditis is the greatest and most common problem. Of the antimonial drugs, one widely used in the clinic is the N-methyl glucamine salt of antimonic acid, frequently called meglumine antimoniate. That compound has been presently employed as a reference drug in evaluation of compounds in the L. donovani-hamster test.

Quinoline derivatives are known to have chemotherapeutic effects against diverse parasites of man. Expecially noteworthy potency against malaria parasites has been demonstrated among 4-aminoquinoline and 8-aminoquinoline structures. In the case of 8-aminoquinoline derivatives, but not 4-aminoquinolines, anti-leishmanial effects have been demonstrated in the Leishmania donovani test in the hamster. Such activity against Leishmania shown by the 8-aminoquinolines is a distinct aspect of anti-parasitic effects, and not related to (e.g.) antimalarial profile thereof. Among series of 8-aminoquinolines, certain 8-amino-6-methoxy-4-methyl-quinolines (otherwise called 8-amino-6-methoxy lepidines) have been identified as markedly more effective than allied compounds lacking the 4-methyl grouping: K. E. Kinnamon, et a., Am. J. Trop. Med. Hyg., 27, 751–757 (1978). The 8-amino-6-methoxylepidines are also subject of the co-pending U.S. patent application Ser. No. 886,024 (Mar. 13, 1978) of K. E. Kinnamon now U.S. Pat. No. 4,209,519. In such work, meglumin antimoniate was used as reference drug. Activity was expressed through use of G index derived from the expression $$G \text{ index} = \frac{SD_{90} \text{ for meglumine antimoniate}}{SD_{90} \text{ for test compound}}$$

wherein $SD_{90}$ refers to the dose causing 90% suppression of L. donovani parasites (amastigote form) present in the livers of infected hamsters. Under standard test conditions—as described by W. L. Hanson, et al. in International J. Parasitol., 7, 443–447 (1977)—primaquine (which is the drug of choice as a radical curvative antimalarial agent) had G index=2.1; 4-methyl primaquine had G index=33. The most active compound was 8-(6-diethylaminohexylamino)-6-methoxylepidine, which had G index=474 by intramuscular route and 708 by oral route. 8-Aminoquinolines have thus been established as effective anti-leishmanial agents in a standard test system.

SUMMARY OF THE INVENTION

It has been established that the lepidine structure (i.e., presence of a 4-methyl grouping on the quinoline moiety) is crucial to high levels of effectiveness among compounds represented by the structural formula (I):

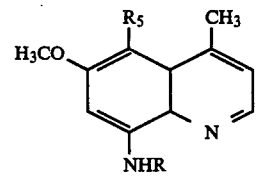

In that structure, Kinnamon (loc. cit.) investigated compounds having $R_5$=H or lower alkoxy function with R being a basically-substituted alkyl grouping containing less than 10 carbon atoms in a straight or branched chain. The basic substituent attached to the alkyl chain was chosen from amino groupings of primary, or secondary, or tertiary amine character, having alkyl, or substituted alkyl, groupings selected as functions attached to the nitrogenous unit.

Presently, subject developments have made alterations in the character of the basically-substituted alkyl grouping R in formula I, when $R_5$ is hydrogen. Prior evidence disclosed by Kinnamon, loc. cit., on the significant value of the alkyl chain being —$(CH_2)_6$— led to the experimental selection of compounds of this invention wherein R represents

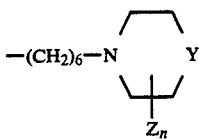

In these compounds, n is an integer from 0 to 2 so that Z when present represents methyl (to form the cis and trans isomers); Y represents —O—, —S—, —S(O)—, —S(O)$_2$—, and —N(R')—; R' represents hydrogen, alkyl, lower alkyl, R" substituted lower alkyl, cycloalkyl, aryl, sulfonyl, saturated 1,4-diazepinyl, lower alkyl N-cyanocarboximidothioate, or —C(O)R'''; R" represents at least one of hydroxy, alkoxy, aralkoxy, amino, lower alkyl substituted amino, phenyl, halogenated phenyl, or sulfonyl; and R''' represents lower alkyl, alkoxy, aralkoxy, amino, lower alkyl substituted amino or aryl substituted amino; and pharmaceutically acceptable salts thereof.

According to this invention, the term alkyl includes a paraffin of greater than 10 carbons while the term lower as applied to an alkyl or alkyl-containing moiety is considered to be a linear or branched chain alkyl moiety of ten or less carbon atoms. The term aryl includes mononuclear groups such as phenyl, phenyl substituted with groups such as lower alkyl, lower alkoxy, lower aralkoxy, amino, lower alkylamino, hydroxy or hydrogen, heterocyclics such as pyridyl or multiring groups such as naphthyls. Members of the foregoing formula class of 8-[6-(N-heterocyclic-substituted)hexylamino]-6-methoxylepidines have been found to exhibit unexpectedly superior activity as anti-leishmanial agents. More particularly, novel 8-quinolinamine derivatives have exhibited outstandingly surprising activity against Leishmania parasites in a standardized animal test system in which a direct comparison was made with the clinically useful anti-leishmanial drug, meglumine antimonate as the reference compound as indicated by the data of Table I. Illustrative of the anti-leishmanial activity exhibited by the lepidine derivatives of this invention can be observed or reference to Examples 5 and 7 (No. 7 and 6, respectively, of Table I) wherein the product of those examples was tested as being 72.3 and 143.2 times as effective as the standard drug (meglumine antimoniate), respectively.

TABLE I

Antileishmanial effects of selected 6-methoxy-4-methyl-N—[-6-(substituted-1-piperazinyl)hexyl]-8-quinolinamines and released compounds.

| | | % Suppression: L. donovani (hamster), (mg/kg) × 2/day | | | | | | | |
|---|---|---|---|---|---|---|---|---|---|
| No. | NR$_1$R$_2$ | 208 | 52 | 13 | 3.25 | 0.81 | 0.2 | 0.05 | G |
| 1 | N(piperazinyl)NCH$_3$ | 99.7(4T) | 100 | 99.7 | 99.3 | 64.7 | | | 26.3 |
| 2 | N(piperazinyl)N-(2,?-dichlorophenyl) | 77.8 | 1$^b$ | | | | | | <1 |
| 3 | N(piperazinyl)N—CH(chlorophenyl)(phenyl) | T$^c$ | 96.8 | 100 | 100 | 70 | | | 22.8 |
| 4 | N(piperazinyl)N(CH$_2$)$_3$N(CH$_3$)$_2$ | T | 99.7 | 65.8 | | | | | 2.2 |

TABLE I-continued

Antileishmanial effects of selected 6-methoxy-4-methyl-N—[-6-(substituted-1-piperazinyl)hexyl]-8-quinolinamines and released compounds.

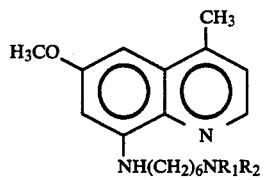

$NH(CH_2)_6NR_1R_2$

| No. | $NR_1R_2$ | % Suppression: L. donovani (hamster), (mg/kg) × 2/day | | | | | | | G |
|---|---|---|---|---|---|---|---|---|---|
| | | 208 | 52 | 13 | 3.25 | 0.81 | 0.2 | 0.05 | |
| 5 | $\bigcap N\ NCH_2CH_2CH_2OH$ | T | 97.8 | 96.3 | | | | | 38.1 |
| 6 | $\bigcap N\ NCH_2CHOHCH_3$ | T | 99.7 | 99.1 | N.A.[d] | | | | 143 |
| 7 | $\bigcap N\ NH$ (with CH_3 groups) | T | 100 | 100 | N.A. | | | | 72.3 |
| 8 | $\bigcap N\ NH$-phenyl | I | | | | | | | <1 |
| 9 | $\bigcap N\ NCCH(C_2H_5)_2$ (C=O) | 5/6T,98.6 | 99.3 | 56.6 | | | | | 2.6 |
| 10 | $\bigcap N\ S$ (with CH_3 groups) | T | 93.7 | 81.1 | | | | | 1.5 |
| 11 | $\bigcap N\ O$ (with CH_3 groups) | T | 99.1 | 99.1 | 98.7 | 61 | | | 24.4 |
| Ia | $N(C_2H_5)_2$ | 6T | 100 | 100 | | 100 | 99.6 | 83.7 | 474 |
| Ib | $\bigcap N\ NCH_2CH_2OH$ | | 100 | 100 | 100 | 97 | 85.8 | | 104 |
| | Meglumine Antimoniate | | 91.3 at | 42 | I | | | | 1 |

TABLE I-continued

Antileishmanial effects of selected 6-methoxy-4-methyl-N—[-6-(substituted-1-piperazinyl)hexyl]-8-quinolinamines and released compounds.

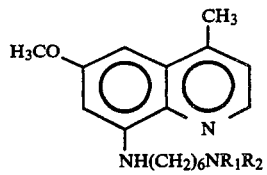

NH(CH$_2$)$_6$NR$_1$R$_2$

| | | % Suppression: L. donovani (hamster), (mg/kg) × 2/day | | | | | | |
|---|---|---|---|---|---|---|---|---|
| No. | NR$_1$R$_2$ | 208 | 52 | 13 | 3.25 | 0.81 | 0.2 | 0.05 | G |
| | | | | | 104 mg/kg | | | | |

G = Glucantime index; Glucantime is the proprietary name for meglumine antimoniate.
$^b$I = inactive.
$^c$T = toxic.
$^d$N.A. = data not available.

Compounds having structure (I) may be administered perorally or parenterally to achieve anti-leishmanial effects. For convenience, such drugs may be administered in the form of the neat chemical bases or as the salt of a pharmaceutically acceptable acid, either inorganic or organic in chemical nature. Non-restrictive examples of inorganic acids suitable for preparation of salts of (I) include: hydrochloride acid; phosphoric acid; nitric acid; sulfamic acid; and sulfuric acid. Suitable organic acids which may be used to form salts of (I) include the following, non-restrictive examples: maleic acid; fumaric acid; citric acid; beta-resorcylic acid; and pamoic acid.

When administered in oral dosage forms, subject anti-leishmanial agents may be incorporated into tablets (single or multi-layer, coated or uncoated), capsules, dragées, and the like. The formulation of such oral dosage forms may advantageously include optional excipients such as lactose, precipitated chalk, dibasic calcium phosphate, microcrystalline cellulose derivatives, maize starch, talc, calcium stearate, or like adjuvant substances whose identity and use are well known in pharmaceutical compounding art. For parenteral administration, aqueous or oily solutions of these lepidine derivatives may be used in a wide range of concentrations. In certain instances, advantage may be gained with use of aqueous suspensions such as may be obtained with ethoxylated sorbitan fatty acid esters, optionally with addition of thickeners such as carboxymethyl cellulose or polyethylenel glycol.

DESCRIPTION OF THE PREFERRED EMBODIMENT

The synthesis of anti-leishmanial agents of structure (I) finds basis in chemical art involving reaction of an 8-aminoquinoline with RX (X being an halogen, usually Cl, Br, or I) to produce the desired 8-NHR quinoline, or by kindred process for conveniently obtaining a basically-substituted sidechain. In certain cases, 8-amino group may be more conveniently interacted with an acid halide type to form an amide, then the amide carbonyl function reduced.

Methods

Assessment of anti-leishmanial effects was done in a model test system based on work of Stauber, et al. [J. Protozool., 5, 269–273 (1958)], and refined by Hanson, et al. (loc. cit.).

Male golden hamsters (*Mesocricetus auratus*), approximately 50–60 gm and the Khartoum strain of *Leishmania donovani* were used in this work. Suspensions of amastigotes for the inoculation of experimental hamsters were prepared by grinding heavily infected hamster spleens in Hanks' balanced salt solution in a Ten Broeck tissue grinder and diluting the suspension to contain $10^7$ amastigotes per 0.2 ml, the amount inoculated into each hamster via the intracardial route. Administration of the drug was initiated 3 days after inoculation and continued through day 6. One day later, the hamsters were weighed, killed, their livers removed and weighed. Liver impressions were prepared, stained with Giemsa's stain and the ratio of the number of amastigotes per host liver cell nucleus determined.

In preparation for the initiation of therapy, the hamsters were weighed and apportioned into groups of 6 to 8. Test compounds were prepared in 0.1% Tween ®80 plus 0.5% hydroxyethylcellulose (HEC-Tween ®) and administered twice daily on days 3 through 6 via the intramuscular, subcutaneous, or oral routes. Compounds were tested at 3 drug dose levels, generally 208, 52 and 13 milligrams per kilogram body weight per day. A group containing a minimum of 6 hamsters were used for each drug dosage level of each test compound. At the time of testing the identity of compounds evaluated was unknown, i.e., compounds were tested "blind." Also included in each experiment was the reference compound, N-methyl-glucamine antimoniate (commercially known as Glucantime ®), at drug dose levels of 104, 13, and 3.25 mg of Sb/kg/day.

Comparison of the suppressive effects of the test compounds with that of the reference compound was made from parasite densities in the liver of each hamster. Total number of parasites in the liver of each hamster were determined from liver impressions according to the method of Stauber et al., 1958.

When the ratio of the number of amastigotes to the number of liver cells had been determined for each hamster in all experimental groups, these data along with initial and final body weights were evaluated with the aid of an IBM 360 computer. A program was devised in which the raw data were accepted by the computer and the total and mean numbers of amastigotes per liver, percent suppression of numbers of amastigotes, and percent body weight change were calculated. Significance tests on the percent suppression of amastigotes were done. The calculations allowed a comparison of the total numbers of amastigotes in the liver of each hamster receiving the reference or test compounds with the mean number of amastigotes in the livers of controls.

A control of the anti-leishmanial activity of each test compound with that of the reference compound was made and a meglumine antimoniate index (relative activity of the test compound to that of the reference drug, which is also called Glucantime ®) for each test compound was calculated by the following formula:

$$\text{Glucantime ® index } (G) = \frac{SD_{90} \text{ for Glucantime ®}}{SD_{90} \text{ for test compound}}$$

For antimony containing compounds, the comparison was based upon the weight of antimony; for non-antimonial containing drugs (presently) the comparison was made based upon the total molecular weight of the compound less that fraction attributable to the salt. The drug dosage levels of active test compounds required for a given degree of effect such as 90% suppression ($SD_{90}$) was estimated graphically by plotting percent parasite suppression vs. milligrams of compound administered per kilogram body weight of the hamster on log paper. When the $SD_{90}$ value could not be obtained because of low activity of the test compound, a lower SD value was used. A G value of greater than one indicates that the test compound was more active than the reference compound, meglumine antimoniate.

The percentage weight gain or loss of treated animals was used as a crude indication of the toxicity of the compound. In addition, the hamsters were observed daily for clinical signs of toxicity such as roughened hair coat, nervous disorders, and death. At necropsy, gross lesions were noted. All of these criteria were used in the determination of the toxicity of the test compound.

The relatively high degree of reproducibility of the screening procedure can be seen from the following data. After 39 weekly experiments, the mean number of amastigotes in the livers of control hamsters was found to be $5.11 \times 10^8$ ($\pm 10^7$ at 95% confidence). Equally good reproducibility was obtained from hamsters receiving 104, 13, or 3.25 mg/kg/day of the reference compound, meglumine antimoniate. The mean number of amastigotes in the livers of these hamsters were $12.1 \times 10^7$ ($\pm 1.1 \times 10^6$), $1.57 \times 10^8$ ($\pm 11.6 \times 10^6$) and $3.5 \times 10^8$ ($\pm 1.30 \times 10^9$). These represent suppressions of 97.6%, 69.2% and 38.3% respectively for the three drug dosage levels.

EXAMPLES

The instant invention is based upon synthesis of 8-[6-(N-heterocyclic-substituted)hexylamino]-6-methoxylepidines as disclosed in the Summary. The subject novel compounds are anti-leishmanial agents, as established in standard testing against *L. donovani* infections in hamsters.

In the following Examples illustrative of the preparation of the various compounds within the scope of this invention, all temperatures are specified as degrees Celsius. The carbon-hydrogen and n.m.r. analytic data provided in the parent application Ser. No. 183,514 referred to above is hereby specifically incorporated by reference.

EXAMPLE 1

6-Methoxy-4-methyl-N-[6-(1-piperazinyl)hexyl]-8-quinolinamine

A.

6-[(6-Methoxy-4-methyl-8-quinolinyl)amino]-1-hexanol

To a stirred mixture of 1.9 g (0.01 mole) of 6-methoxy-4-methyl-8-quinolinamine and 1.4 g (0.01 mole) of 6-chlorohexanol at 150° was added portionwise over one hr 1.4 ml (0.01 mole) of triethylamine. The mixture was stirred for 1 hr at the same temperature, and then 0.8 g (0.0056 mole) of 1-chlorohexanol was added, followed by the portionwise addition of 0.8 (0.0056 mole) of triethylamine. The mixture was stirred for 1 hr and the procedure was repeated with 0.5 g (0.0037 mole) of 1-chlorohexanol and 0.5 ml of triethylamine. After the mixture was stirred an additional hr, the mixture was allowed to cool, diluted with acetone, filtered, and concentrated to dryness in vacuo. The residue was dissolved in dichloromethane and chromatographed over 70 g of silica gel first with 500 ml of dichloromethane and then with the following solutions of ethyl acetate in dichloromethane: 5% (500 ml), 10% (1 liter), 15% (500 ml), and finally 20% (500 ml). Fractions of the 20% eluant containing the product, Rf(silica—ethyl acetate)=0.3, were combined and concentrated to dryness in vacuo. Recrystallization from 2-propanol afforded 1.6 g (55%) of the title compound, mp 97°–99°.

B.

N-(6-Chlorohexyl)-6-methoxy-4-methyl-8-quinolinamine

To a cold (0°–5°) suspension of 3 (0.0104 mole) of 6-[(6-methoxy-4-methyl)-8-quinolinyl)amino]-1-hexanol in 30 ml of dichloromethane was dropwise 0.8 ml (0.012 mole) of thionyl chloride in 30 ml of dichloromethane. The stirred mixture was allowed to warm to room temperature overnight and then concentrated to dryness in vacuo. The residue was then taken up in iced water and ether and treated with concentrated ammonia until alkaline. The ether layer was separated, washed, dried, and evaporated to dryness to afford 3 g (95%, 0.01 mole) of crude N-(6-chlorohexyl)-6-methoxy-4-methyl-8-quinolinamine.

C.

6-Methoxy-4-methyl-N-[6-(1-piperazinyl)hexyl]-8-quinolinamine, trihydrochloride

A solution of 6.2 g (0.02 mole) of crude N-(6-chlorohexyl)-6-methoxy-4-methyl-8-quinolinamine in 75 ml of toluene was added dropwise to a stirred, hot suspension of 25 g (0.29 mole) of piperazine in 25 ml of toluene. The mixture was distilled until the internal temperature rose to 130°, allowed to cool, and taken up in a mixture of water and dichloromethane. The organic layer was separated, washed again, dried over anhydrous magnesium sulfate and concentrated to dryness in vacuo. The residual brown oil was chromatographed over 200 g of silica gel first with ethyl acetate and then with 500 ml each of the following solutions of methanol in ethyl acetate: 4%, 8%, 12% 16%, 20% and 25%. The eluant which appeared to contain only the product, Rf (silica—25 methanol:75 ethyl acetate:1 triethylamine)=0.05 was concentrated to dryness in vacuo. The residue was triturated with ether and filtered to remove 1 g of the bis product, mp 126°–128°, and concentrated again. The residue was dissolved in hot 2-propanol, filtered to remove haze and treated with a saturated solution of hydrogen chloride in 2-propanol. The resulting precipitate was collected, dried overnight at 60° in vacuo and allowed to air-equilibrate to afford 5.8 (60%) of the title compound, mp 245°–247° (dec) with prior sintering at 125°. The NMR spectrum confirmed the presence of 2-propanol.

EXAMPLE 2

6-Methoxy-4-methyl N-[6-(4-methyl-1-piperazinyl)-hexyl]-8-quinolinamine

A.

6-Bromo-N-(6-methoxy-4-methyl-8-quinolinyl)-hexanamide

6-Methoxy-4-methyl-8-quinolinamine was converted to the title amide by reaction with 6-bromohexanoyl chloride in the usual manner.

B.

N-(6-Methoxy-4-methyl-8-quinolinyl)-4-methyl-1-piperazinehexanamide

A mixture of 5.5 g (0.015 mole) of 6-bromo-N-(6-methoxy-4-methyl-8-quinolinyl)hexanamide and 1.8 g (0.018 mole) of N-methylpiperazine in 70 ml of benzene was heated under reflux for 20 hr, treated with 2 ml of triethylamine, and heated for an additional 24 hr. The mixture was allowed to cool, filtered and the filtrate was washed with water, dried and concentrated to dryness in vacuo. The residue was recrystallized twice from n-hexane containing a little toluene and then dried in vacuo at 68° to afford 3.1 g (53%) of the title compound, mp 104°–107°.

C.

6-Methoxy-4-methyl-N-[6-(4-methyl-1-piperazinyl)hexyl]-8-quinolinamine

A cold (−40°) slurry of 1.0 g (0.0015 mole) of anhydrous aluminum chloride in 60 ml of tetrahydrofuran was added to a cold (−40°) suspension of 0.8 g (0.021 mole) of lithium aluminum hydride in 40 ml of tetrahydrofuran. The mixture was stirred and allowed to warm up to −20°. To it was added dropwise a solution of 2.0 g (0.0052 mole) of N-(6-methoxy-4-methyl-8-quinolinyl)-4-methyl-1-piperazine-hexanamide in 50 ml of tetrahydrofuran. The mixture was stirred for 1 hr and stored at 4° overnight. To it was added dropwise 4 ml of 30% sodium hydroxide solution and enough water to clarify the supernatant. The supernatant was decanted and the residual sticky precipitate was washed with tetrahydrofuran. The wash and supernatant were combined, concentrated in vacuo to remove the tetrahydrofuran and taken up in dichloromethane and water. The dichloromethane layer was separated, washed with water and saturated sodium chloride solution, dried over anhydrous magnesium sulfate, filtered and concentrated to dryness in vacuo.

A solution of the residue in 2-propanol was treated with a saturated solution of hydrogen chloride in 2-propanol. The resuting gelatinous precipitate was collected, washed with 2-propanol and ether, dried overnight at 55° in vacuo and allowed to air-equilibrate to afford 2.0 g (74%) of the title compound, m.p. 241°–244°, NMR confirmed the presence of 0.3 mole of 2-propanol.

EXAMPLE 3

N-[6-(4-Dodecyl-1-piperazinyl)-hexyl]-6-methoxy-4-methyl-8-quinolinamine

Crude N-(6-chlorohexyl)-6-methoxy-4-methyl-8-quinolinamine (Example 1B), 3.0 g (0.01 mole) was combined with 2.3 g (0.0076 mole) of 84% (by VPC) 1-dodecylpiperazine and heated at 130° with occasional stirring for 3 hr. During this period 3 ml of triethylamine was added in portions. The mixture was allowed to cool, diluted with ether, washed with 1% sodium hydroxide and with water, dried over anhydrous magnesium sulfate, filtered and concentrated in vacuo to dryness. The residue (5 g) was chromatographed over 200 g of silica gel first with 1 liter of dichloromethane and then with 1 liter each of the following solutions of methanol in dichloromethane: 1%, 1.5%, 2%, 2.5%, 3%, 4% and 5%. Fractions containing material with Rf's (silica—ethylacetate)=0.64 and (silica 5% methanol/dichloromethane)=0.95 were combined and concentrated to dryness in vacuo. Recrystallization from hexane afforded 0.9 g (30%) of the unreacted intermediate N-(6-chlorohexyl)-6-methoxy-4-methyl-8-quinolinamine, mp 64°–66°. The chlorination was repeated as described above with 23.2 g (0.8 mole) of the hexanol and 9.2 ml of thionyl chloride. The concentrated reaction mixture was made alkaline, extracted with ether, concentrated, and then chromatographed over 800 g of silica gel with dichloromethane to afford 18 g of crude product. Recrystallization from hexane afforded 17.1 g (70%) of N-(6-chlorohexyl)-6-methoxy-4-methyl-8-quinolinamine, mp 66°.

Fractions containing material with R$_f$(silica-5% methanol/dichloromethane)=0.33 were combined and concentrated to dryness in vacuo to give 2 g of material. Recrystallization first from hexane and then from 2-propanol afforded 0.85 g (22%) of N-[6-(4-dodecyl-1-piperazinyl)hexyl]-6-methoxy-4-methyl-8-quinolinamine, mp 53°–55°.

EXAMPLE 4

6-Methoxy-4-methyl-N-[6-[2-methyl-4-(3-methylbutyl-1-piperazinyl]hexyl]-8-quinolinamine

A.

N-(6-Methoxy-4-methyl-8-quinolinyl)2-methyl-4-(3-methylbutyl)-1-piperazinehexanamide A mixture of 6 g (0.0164 mole) of 6-bromo-N-(6-methoxy-4-methyl-8-quinolinyl)hexanamide, 3 g (0.017 mole) of 1-(3-methyl-butyl)-3-methylpiperazine and 3 ml of triethylamine in 100 ml of benzene was heated under reflux for 30 hr, allowed to cool and filtered to remove triethylamine hydrobromide. The filtrate was combined with 1 ml of triethylamine and heated under reflux for 28 hr. The cooled reaction mixture was combined with water and additional benzene. The benzene layer was separated, washed, dried and concentrated to dryness. The residue dissolved in ethyl acetate and chromatographed over 200 g of silica gel first with ethyl acetate, then with a 7% solution of methanol in ethyl acetate and finally with a 10% solution of methanol in ethyl acetate. Fractions containing product, R$_f$(15% methanol/ethyl acetate)=0.12, were combined and concentrated to afford 3.3 g (44%) of the desired product as an oil, which was used in the next step without further purification. The structure was confirmed by IR and NMR spectra.

B.
6-Methoxy-4-methyl-N-[6-[2-methyl-4-(3-methylbutyl)-1-piperazinyl]-hexyl]-8-quinolinamine, hydrochloride A cold (−40°) slurry of 1.4 g (0.0105 mole) of anhydrous aluminum chloride in 50 ml of tetrahydrofuran was added to a cold (−40°) suspension of 1.1 g (0.029 mole) of lithium aluminum hydride in 50 ml of tetrahydrofuran and the mixture was stirred, allowing the temperature to rise to −20°. To it was added dropwise a solution of 3.2 g (0.007 mole) of N-(6-methoxy-4-methyl-8-quinolinyl)-2-methyl-4-(3-methylbutyl)-1-piperazinehexanamide in 70 ml of tetrahydrofuran. The mixture was stirred for 3 hr, allowing the temperature to rise to 10°, and it was then treated with 5 ml of 30% sodium hydroxide and enough water to clarify the supernatant. The supernatant was decanted and the residual gum was washed with tetrahydrofuran. The supernatant and wash were combined, concentrated in vacuo to remove most of tetrahydrofuran and combined with ether and water. The ether layer was separated, washed, dried, and concentrated to dryness. The residual oil was chromatographed over 75 g of silica gel, eluting first with ethyl acetate, then with 5% solution and finally a 10% solution of methanol in ethyl acetate. Those fractions containing pure product, $R_f$(silica gel—75 ethyl acetate: 25 methanol:1 triethylamine)=0.4, were combined and concentrated to dryness in vacuo. Trituration with a 10% solution of hydrogen chloride in 2-propanol afforded a gold solid. The material was collected, washed with ether, dried in vacuo at 95°, and air-equilibrated to give 2.3 g (60%) of the title compound.

EXAMPLE 5
N-[6-(3,5-Dimethyl-1-piperazinyl)hexyl]-6-methoxy-4-methyl-8-quinolinamine

A.
N-(6-Methoxy-4-methyl-8-quinolinyl)-3,5-dimethyl-1-piperazine-hexanamide A mixture of 5.5 g (0.015 mole) of 6-bromo-N-(6-methoxy-4-methyl-8-quinolinyl)hexanamide and 3.4 g (0.03 mole) of 2,6-dimethylpiperazine in 80 ml of benzene was heated under reflux for 21 hr, treated with 2 ml of triethylamine, and heated for an additional 4 hr. The mixture was allowed to cool, diluted with water and toluene, and made strongly basic with 50% sodium hydroxide solution. The organic layer was washed, dried and concentrated to dryness in vacuo. Recrystallization from hexane containing a little toluene afforded 5 g (83%) of the title compound, mp 94°–96°.
Anal. Calcd for $C_{23}H_{34}N_4O_2$: C, 69.31; H, 8.60; N, 14.06. Found: C, 68.98; H, 8.65; N, 13.65.

B.
N-[6-(3,5-Dimethyl-1-piperazinyl)hexyl]-6-methoxy-4-methyl-8-quinolinamine, trihydrochloride A cold slurry (−40°) of 1.5 g (0.011 mole) of anhydrous aluminum chloride in 80 ml of tetrahydrofuran was added to a cold (−40°) suspension of 1.1 g (0.029 mole) of lithium aluminum hydride in 40 ml of tetrahydrofuran and the mixture was stirred and allowed to warm to −20°. To it was added dropwise a solution of 3.54 g (0.0085 mole) of N-(6-methoxy-4-methyl-8-quinolinyl)-3,5-dimethyl-1-piperazinehexanamide in 100 ml of tetrahydrofuran. The reaction mixture was stirred for 1 hr and stored at 4° overnight. Then to the mixture were added 6.5 ml of 30% sodium hydroxide solution and enough water to cause a sticky precipitate to separate. The supernatant was filtered, concentrated in vacuo to remove most of the tetrahydrofuran and diluted with dichloromethane and water. The dichloromethane was separated, washed, dried, and concentrated in vacuo. The residue was chromatographed over 175 g of silica gel eluting with a liter each of the following solutions of methanol in ethyl acetate: 1%, 3%, 5%, 7%, 9% and 10%. Fractions containing product, $R_f$(silica—75 parts of ethyl acetate:25 parts of methanol:1 part of triethylamine)=0.33, were combined and concentrated to dryness. A solution of the residue in 2-propanol was treated with an excess of a 15% solution of hydrogen chloride in 2-propanol and chilled overnight. The resulting precipitate was collected, washed with 2-propanol and ether, dried in vacuo at 55° and allowed to air-equilibrate to afford 1.9 g (41%) of the title compound, mp 120°–180° (dec).

EXAMPLE 6
4-[6-[(6-Methoxy-4-methyl-8-quinolinyl)amino]-hexyl]-1-piperazinepropanol

A.
4-(3-Hydroxypropyl)-N-(6-methoxy-4-methyl-8-quinolinyl)-1-piperazine-hexanamide A mixture of 4.3 g (0.012 mole) of 6-bromo-N-(6-methoxy-4-methyl-8-quinolinyl)hexanamide and 3.5 g (0.024 mole) of 1-piperazinepropanol was heated at 120° for 2 hr and allowed to cool. The mixture was diluted with ethyl acetate and excess triethylamine, washed with water, dried over anhydrous magnesium sulfate, filtered and concentrated in vacuo to dryness to afford 4.9 g (96%) of the desired compound as a gum. The IR and NMR ($CDCl_3$) were consistent with the assigned structure.

B.
4-[6-[(6-Methoxy-4-methyl-8-quinolinyl)amino]hexyl]-1-piperazine-propanol A cold (−40°) slurry of 1.8 g (0.0135 mole) of anhydrous aluminum chloride in 60 ml of tetrahydrofuran was added to an equally cold suspension of 1.5 g (0.039 mole) of lithium aluminum hydride in 30 ml of tetrahydrofuran. The mixture was stirred and allowed to warm to −10°. To it was added dropwise a solution of 4.4 g (0.0103 mole) of 4-(3-hydroxypropyl)-N-(6-methoxy-4-methyl-8-quinolinyl)-1-piperazinehexanamide in 15 ml of tetrahydrofuran. The mixture was stirred for 2 hr, then treated with 7 ml of 30% sodium hydroxide solution and enough water to clarify the supernatant and finally filtered through supercell. The filtrate was concentrated in vacuo to remove tetrahydrofuran, diluted with dichloromethane, washed with water, dried, and concentrated to dryness. The residue was chromatographed over 200 g of silica gel with a 15:84:1 mixture of methanol:ethyl acetate-triethylamine. That portion of the eluant containing the product, $R_f$(silica—25:74:1 mixture of methanol:ethyl acetate:triethylamine)=0.33, was concentrated to dryness in vacuo. Recrystallization of the residue from 2-propanol afforded 2.1 g (49%) of the title compound, mp 100°–102°.

EXAMPLE 7

4-[6-[(6-Methoxy-4-methyl-8-quinolinyl)amino]-hexyl]-α-methyl-1-piperazineethanol A solution of 2.0 g (0.004 mole) of 6-methoxy-4-methyl-N-[6-1-piperazinyl)hexyl]-8-quinolinamine, trihydrochloride, compd with 2-propanol (1:0.2), hemihydrate (Example 1) in water was made basic with ammonium hydroxide and extracted with dichloromethane. The dichloromethane was washed, dried over anhydrous magnesium sulfate, filtered and concentrated to dryness in vacuo. A mixture of the residual brown oil and 1.3 ml (0.016 mole) of 1-chloro-2-propanol was heated at 130° for 3 hr, allowed to cool, and taken up in a mixture of dichloromethane and dilute ammonium hydroxide. The dichloromethane was washed, dried, and concentrated to dryness in vacuo. The residual oil was chromatographed over 70 g of silica gel with 14% methanol in ethyl acetate to afford 0.8 g of the product, Rf[silica—ethyl acetate:methanol:triethylamine (75:25:1)]=0.33. A solution of this material in 2-propanol was treated with a saturated solution of hydrogen chloride in 2-propanol. The resulting precipitate was collected, washed with 2-propanol and ether, dried in vacuo at 45° for 55 hr and allowed to air-equilibrate for 18 hr to afford 1.0 g (46%) of the title compound, mp 80°-100°, resolidify, 245° (dec).

EXAMPLE 8

N-[6-[4-[2-Diphenylmethoxy)ethyl]-1-piperazinyl]-hexyl]-6-methoxy-4-methyl-8-quinolinamine, trihydrochloride, hydrate (1:0.3)

A. 4-[2-(Diphenylmethoxy)ethyl]-N-(6-methoxy-4-methyl-8-quinolinyl)-1-piperazinehexanamide A mixture of 2.6 g (0.007 mole) of 1-[2-diphenylmethoxy)ethyl]piperazine dihydrochloride, 2.4 g (0.0065 mole) of 6-bromo-N-(6-methoxy-4-methyl-8-quinolinyl)hexanamide, and 2 ml (0.014 mole) of triethylamine in 100 ml of benzene was heated under reflux for 48 hr, allowed to cool, and filtered to remove triethylamine hydrohalide salts. The filtrate was combined with 1 ml of triethylamine, heated under reflux for 24 hr, allowed to cool, washed with water and saturated sodium chloride solution, dried over anhydrous magnesium sulfate, filtered, and concentrated to dryness in vacuo. The residual oil was chromatographed over 150 g of silica gel first with dichloromethane, then with a 4% solution and finally with a 7% solution of methanol in dichloromethane (1 l each), to afford 2.3 g (60%) of product. TLC(silica—10% methanol/ethyl acetate) demonstrated that the product, Rf=0.16, was contaminated with a small amount of the starting bromohexanamide, Rf=0.87. The material was used in the next step without further purification.

B. N-[6-[4-[2-Diphenylmethoxy)ethyl]-1-piperazinyl]hexyl]-6-methoxy-4-methyl-8-quinolinamine, trihydrochloride, hydrate (1:0.3)

To a cold (−40°) suspension of 0.7g (0.018 mole) of lithium aluminum hydride in 30 ml of tetrahydrofuran was added a cold (−40°) slurry of 0.9 g (0.007 mole) of anhydrous aluminum chloride in 50 ml of tetrahydrofuran. The mixture was allowed to warm to −20° and to it was added dropwise a solution of 2.2 g (0.0038 mole) of 4-[2-(diphenylmethoxy)ethyl]-N-(6-methoxy-4-methyl-8-quinolinyl)-1-piperazinehexanamide in 60 ml of tetrahydrofuran. The mixture was stirred for 2 hr, allowing the temperature to rise to 5°. To the mixture was added 3 ml of 30% sodium hydroxide solution and enough water to clarify the supernatant which was then decanted. The sticky white precipitate that remained was washed with tetrahydrofuran. The wash and original supernatant were combined, concentrated in vacuo to remove most of the tetrahydrofuran and taken up in water and dichloromethane. The dichloromethane was separated, washed, dried, and concentrated to dryness in vacuo. Trituration with a 5% solution of hydrogen chloride in 2-propanol produced a gold solid. The material was collected, washed with 2-propanol and ether and dried at 85° in vacuo to afford 2.1 g (82%) of the title compound, mp 138°-145°.

EXAMPLE 9

N-[6-[4-(2-(Ethylsulfonyl)ethyl]-1-piperazinyl]-hexyl]-6-methoxy-4-methyl-8-quinolinamine

A. 2-(Ethylsulfonyl)ethanol 1,4-methylbenzenesulfonate-

To a cold (−5°) solution to 10 g (0.072 mole) of 2-(ethylsulfonyl)ethanol in 25 ml of pyridine was added 13.8 g (0.072 mole) of 4-methylbenzenesulfonychloride in portions. The mixture was stirred at 0° for 3 hr, then treated with 36 ml of water in a dropwise fashion and finally diluted with dichloromethane. The dichloromethane layer was separated, washed with 90 ml of 2N hydrochloric acid and then with water, dried over anhyrous magnexium sulfate and concentrated to dryness under vacuum. The residue was triturated with hexane to afford 15.6 g (73.5% of the desired product, mp 55°-57Z° (lit. reports mp 57°-59°).

B. 4-[2-(Ethylsulfonyl)ethyl]-1-piperazinecarboxylic acid, phenylmethyl ester To a solution of 6.6 g (0.03 mole) of 1-piperazinecarboxylic acid, phenylmethyl ester in 100 ml of N,N-dimethylformamide was added, in portions, 1.44 g (0.03 mole) of a 50% sodium hydride suspension in mineral oil. The mixture was heated at 50° for 1 hr and allowed to cool slightly. To it was added dropwise a solution of 8.8 g (0.003 mole) of 2-(ethylsulfonyl)ethanol, 4-methylbenzenesulfonate in 30 ml of N,N-dimethylformamide. The mixture was heated at 50° for 1 hr, allowed to cool, concentrated under vacuum to one-half the original volume, allowed to stand for four days and then concentrated to a paste. The paste was diluted with ether and the suspension filtered to remove insoluble salts. The filtrate was concentrated and chromatographed over 250 g of silica gel with 1 l each of the following solutions of methanol in ethyl acetate: 1.5%, 3% and 15%. That portion of the eluent containing the product, Rf(silica—10% methanol/ethyl acetate)=0.7, was concentrated to dryness under vacuum to afford 8.3 g (81%) of the desired product as an oil. The IR and NMR spectra were consistent with the assigned structure.

C. 1-[2-(Ethylsulfonyl)ethyl]piperazine, dihydrobromide

A solution of 0.58 g (0.0017 mole) of 4-[2-(ethylsulfony)ethyl]-1-piperazinecarbonylic acid, phenylethyl ester in 4 ml of acetic acid and 1 ml of 48% hydrobromic acid was heated on the steam bath for 35 min and allowed to cool to afford 0.5 g (79%) of the desired product, mp 265°–267° (dec).

D. N-[6-[4-[2-(Ethylsulfonyl)ethyl]-1-piperazinyl]hexyl]-6-methoxy-4-methyl-8-quinolinamine A mixture of 3.1 g (0.01 mole) of N-(6-chlorohexyl)-6-methoxy-4-methyl-8-quinolinamine and 4.1 g (0.011 mole) of 1-[2-(ethylsulfonyl)ethyl]piperazine, dihydrobromide in 30 ml of N,N-dimethylformamide was heated at 120° under a stream of nitrogen for 1 hr, treated with 3 ml of triethylamine, heated for 4 hr and allowed to cool. The reaction mixture was filtered to remove salt and concentrated to dryness under vacuum. The residue was dissolved in dichloromethane and the solution was washed with water, dried and concentrated. Chromatography over 200 g of silica gel with a 1:5:94 mixture of triethylamine:methanol:ethyl acetate afforded 3.5 g of product, Rf(silica—10% methanol/ethyl acetate)=0.36. The material was triturated with hexane and then recrystallized from a mixture of 150 ml of hexane and 100 ml of 2-propanol to afford 3.0 g (61%) of the title compound, mp 70–72. The NMR verified the presence of 0.2 mole of hexane.

EXAMPLE 10

3-[4-[6-[[6-Methoxy-4-methyl-8-quinolinyl]amino]hexyl]-1-piperazinyl]-1,2-propanediol A mixture of 3 g (0.008 mole) of 6-methoxy-4-methyl-N-[6-(1-piperazinyl)hexyl]-8-quinolinamine (Example 1) and 0.72 ml (0.008 mole) of 3-chloro-1,2-propanediol was heated at 120° for 2 hours. An additional 0.2 ml of 3-chloro-1,2-propanediol and 1 ml of triethylamine were added and the mixture was heated at 130° for 3 hr and allowed to cool. The reaction mixture was diluted with ethyl acetate, washed with water and saturated sodium chloride solution, dried over anhydrous magnesium sulfate, filtered and concentrated to dryness in vacuo. The residual oil was chromatographed over 200 g of silica gel, eluting first with one liter of a 1:15:84 mixture of triethylamine:methanol:ethyl acetate and then with a 1:20:79 mixture of the same solvents. That portion of the eluant containing fairly pure product Rf(silica—25 parts of methanol:75 parts of ethyl acetate:1 part of triethylamine)=0.26 was concentrated to dryness, taken up in 2-propanol and treated with an excess of a 17% solution of hydrogen chloride in 2-propanol to afford 0.7 g of product. That portion of the eluant containing contaminated product was concentrated and rechromatographed over 50 g of silica with a 1:15:84 mixture of triethyl amine:methanol:ethyl acetate and the product was isolated as described above. The two crops were combined and recrystallized from ethanol to afford 1.0 g (23%) of the title compound, mp. 237°–241° (dec) with prior sintering.

EXAMPLE 11

N-[6-[4-[3-(Dimethylamino)propyl]-1-piperazinyl]-hexyl]-6-methoxy-4-methyl-8-quinolinamine

A. 1-[3-(Dimethylamino)propyl]piperazine

A mixture of 100 g (1.2 mole) of piperazine, 72 g (0.455 mole) of 3-chloro-N,N-dimethylpropanamine, hydrochloride and 110 g (1.3 mole) of sodium bicarbonate in 500 ml of ethanol was heated under reflux for 7 hr, allowed to cool, filtered and concentrated to dryness under vacuum. The concentrate was slurried in dichloromethane and filtered. The filerate was concentrated and then distilled under water pump pressure (~5 mm) to afford 34 g (44%) of the desired product, bp 100°–102°/5 mm.

B. N-[6-[4-[3-(Dimethylamino)propyl]-1-piperazinyl]hexyl]-6-methoxy-4-methyl-8-quinolinamine,tetrahydrochloride A mixture of 3.1 g (0.01 mole) of N-(6-chlorohexyl)-6-methoxy-4-methyl-8-quinolinamine and 2.0 g (0.012 mole) of 1-[3-(dimethylamino)propyl]piperazine was heated at 120° under a stream of nitrogen with occasional stirring for 4 hr, allowed to cool and taken up in dichloromethane. The dichloromethane was washed with water and with saturated sodium chloride solution, dried over anhydrous magnesium sulfate, filtered and concentrated under vacuum to dryness. The residue was chromatographed over 300 g of alumina (Alcoa F-20) with 1 l of a 1:1 dichloromethane:ethyl acetate mixture and then with the following solutions of methanol in the same solvent mixture: first 1.5% (0.5 l) and then 10% (1 l). That portion of the eluent containing the product, Rf(alumina—10% methanol in ethyl acetate)=0.3, was concentrated to an oil. A solution of this oil in 2-propanol was filtered and treated with 7 ml of a 12% solution of hydrogen chloride in 2-propanol to afford an orange, gelatinous precipitate. The precipitate was collected, recrystallized from ethanol, dried, crushed and dried again under vacuum at 70° to afford 1.9 g (32%) of the title compound. The NMR spectrum demonstrated the presence of 0.2 mole of ethanol.

EXAMPLE 12 alpha[(Diethylamino)methyl]-4-[6-[(6-methoxy-4-methyl-8-quinolinyl)amino]hexyl]-1-piperazineethanol

A. Diethyloxiranemethanamine

A mixture of 92.5 g (1 mole) of epichlorohydrin, 186.4 g (1.2 mole) of diethylamine and 4 ml of water was stirred for 6.5 hr, while the temperature was maintained at 28°–32° with intermittent cooling. The reaction mixture was cooled to 20°, and a solution of 56 g of sodium hydroxide in 912 ml of water was added with vigorous stirring. During the addition the temperature was maintained at 20°–25°. The mixture was stirred for 40 min and then poured into 200 ml of H$_2$O. The upper layer was separated and the lower aqueous layer was extracted twice with ether. The extracts were combined with the oil, dried overnight over potassium hydroxide in the cold and filtered. The filtrate was distilled to give 74.6 g (58%) of the desired product, bp (20 mm)=53°–58°. The VPC indicated that the material consisted of 99% of the single component and the NMR was consistent with the assigned structure.

B. α-[(Diethylamino)methyl]-4-[6-[(6-methoxy-4-methyl-8-quinolinyl)amino]hexyl]-1-piperazineethanol A mixture of 3.5 g (0.009 mole) of 6-methoxy-4-methyl-N-[6-(1-piperazinyl)hexyl]-8-quinolinamine (Example 1) and 2.5 g (0.019 mole) of diethyloxiranemethanamine was heated on the steambath for 4 hr, allowed to cool, diluted with dichloromethane, washed with water, dried and concentrated to dryness in vacuo. The residue was chromatographed over 300 g of silica gel with 15% methanol and 1% triethylamine in ethyl acetate. That portion of the eluant containing the product, Rf(silica—75 parts of ethyl acetate:25 parts of methanol:1 part of triethylamine)=0.12, was concentrated in vacuo. The residual oil was dissolved in 2-propanol and treated with an excess of hydrogen chloride in 2-propanol. The resulting precipitate was collected, washed with 2-propanol, dried at 80° in vacuo, crushed, and again dried at 80° to afford 1.8 g (30% yield) of the title compound, mp. 241°-244° (dec).

EXAMPLE 13

N-[6-(4-Cyclohexyl-1-piperazinyl)hexyl]-6-methoxy-4-methyl-8-quinolinamine

A.

4-Cyclohexyl-N-(6-methoxy-4-methyl-8-quinolinyl)-1-piperazine-hexanamide

A mixture of 3.7 g (0.01 mole) of 6-bromo-N-(6-methoxy-4-methyl-8-quinolinyl)hexanamide, 3.4 g (0.0105 mole) of 1-cyclo-hexylpiperazine, dihydrobromide, and 4.2 ml (0.03 mole) of triethylamine in 100 ml of benzene was heated under reflux for 40 hr, allowed to cool, filtered and concentrated. The residue was chromatographed over 150 g of silica gel first with dichloromethane and then with 500 ml each of the following solutions of methanol in dichloromethane: 2%, 4%, 6%, 10% and 15%. The fractions containing the product [Rf(silica—75 ethyl acetate:25 methanol:1 triethylamine)=0.6] were concentrated to provide 3.4 g (75%) of clean material and 0.8 g (18%) which was slightly contaminated according to TLC. The contaminated material was combined with 0.8 g of the purer material and recrystallized first from 2-propanol and then from 2-propanol-water to afford 0.7 g (44% recovery) of analytical material, mp 109°-110°.

4-methyl-8-quinolinamine

A mixture of 2.6 g of crude 4-cyclohexyl-N-(6-methoxy-4-methyl-8-quinolinyl)-1-piperazinehexanamide in 100 ml of tetrahydrofuran was filtered to remove 0.3 g of white insoluble material. The filtrate, now containing 2.3 g (0.005 mole) of starting material was added dropwise to a cold (−20°) mixture of aluminum chloride and lithium aluminum hydride which had been prepared by adding a cold (−40°) slurry of 1.1 g (0.008 mole) of aluminum chloride in 75 ml of tetrahydrofuran to an equally cold suspension of 0.9 g (0.02 mole) of lithium aluminum hydride in 50 ml of tetrahydrofuran and allowing the mixture to warm to −20°. The reaction mixture was stirred at −20° to 0° for 3 hr and allowed to stand overnight at 4°. To the stirred mixture was added 3.8 ml of 30% sodium hydroxide and enough water to clarify the supernatant, which was then decanted. The residual sticky precipitate was washed with tetrahydrofuran. The supernatant and wash were combined, concentrated in vacuo to remove most of the tetrahydrofuran and taken up in water and ether. The ether layer was washed, dried and concentrated, leaving 2 g of crude product. Recrystallization from 2-propanol afforded 0.9 g (43%) of the purified material, mp 68°-70°.

EXAMPLE 14

N-[6-[4-[(4-Chlorophenyl)phenylmethyl]-1-piperazinyl]-hexyl]-6-methoxy-4-methyl-8-quinolinamine

A.

4-[(4-Chlorophenyl)phenylmethyl]-N-(6-methoxy-4-methyl-8-quinolinyl)-1-piperazinehexanamide A mixture of 3 g (0.0081 mole) of 6-bromo-N-(6-methoxy-4-methyl-8-quinolinyl)hexanamide, 2.4 g (0.008 mole) of 1-[(4-chlorophenyl)phenylmethyl]piperazine, and 2 ml of triethylamine in 70 ml of benzene was heated under reflux for 28 hr, allowed to cool, filtered, and concentrated to dryness in vacuo. The residue was dissolved in a minimal amount of dichloromethane and then chromatographed over 150 g of silica gel eluting first with 500 ml of dichloromethane, then with 500 ml portions of the following solutions of methanol in dichloromethane: 1%, 2%, 3%, 4% and finally with 1 l of 5% methanol in dichloromethane. Concentration of appropriate fractions afforded 1.4 g (30%) of product, Rf(silica—10% methanol/dichloromethane)=0.5 and 1.6 g (35%) of product contaminated with the bromohexanamide starting material, Rf=0.97 (total yield=65%). The two crops were combined and used in the next reaction. NMR and IR of the clean material were consistent with the structure.

B.

N-[6-[4-[(4-Chlorophenyl)phenylmethyl]-1-piperazinyl]hexyl]-6-methoxy-4-methyl-8-quinolinamine,hydrochloride(1:2.2)

A cold (−40°) slurry of 1 g (0.0075 mole) of anhydrous aluminum chloride in 30 ml of tetrahydrofuran was added to a cold (−30°) suspension of 0.7 g (0.018 mole) of lithium aluminum hydride in 30 ml of tetrahydrofuran. The mixture was stirred and allowed to warm to −20° and then to it was added dropwise a solution of 2.9 g (0.005 mole) of 4-[(4-chlorophenyl)phenylmethyl]-N-(6-methoxy-4-methyl-8-quinolinyl)-1-piperazinehexanamide in 30 ml of tetrahydrofuran. The mixture was allowed to warm to room temperature over a 3 hr period and then stored in the cold (4°) overnight. To the stirred reaction mixture was added 3.5 ml of 30% sodium hydroxide and enough water to clarify the supernatant, which was then decanted. The residual sticky precipitate was washed with tetrahydrofuran. The supernatant and wash were combined, concentrated in vacuo to remove tetrahydrofuran, and taken up in dichloromethane and water. The dichloromethane was washed, dried, concentrated and chromatographed over 80 g of silica gel with ethyl acetate. Fractions containing product, Rf(silica—ethyl acetate)=0.2, were combined and concentrated. Trituration of the residue with 2-propanol saturated with hydrogen chloride afforded a yellow precipitate. This material was dissolved in hot 2-propanol and diluted with water to give 0.2 g of white solid which was discarded. The filtrate was concentrated, taken up in water and dichloromethane, and treated with excess ammonium hydroxide. The dichloromethane was separated, washed, dried and concentrated. The residue was chromatographed over 70 g of silica gel first with dichloromethane, then with a 1% solution, and finally with a 2% solution of methanol in dichloromethane. Fractions containing pure product were combined and concentrated to dryness. Trituration of the residue with 2-propanol saturated with hydrogen chloride afforded a yellow precipitate which was collected, washed with cold 2-propanol and ether, and dried to give 1.2 g (38%) of the title compound, mp 180°-185° (dec).

EXAMPLE 15

N-[6-[4-(3,4-Dichlorophenyl)-1-piperazinyl]hexyl]-6-methoxy-4-methyl-8-quinolinamine

A.

4-(3,4-Dichlorophenyl)-N-(6-methoxy-4-methyl-8-quinolinyl)-1-piperazinehexanamide A mixture of 4.3 g (0.012 mole) of 6-bromo-N-(6-methoxy-4-methyl-8-quinolinyl)hexanamide, 4.0 g (0.0128 mole) of 1-(3,4-dichlorophenyl)piperazine, hydrobromide and 2 ml (0.014 mole) of triethylamine in 100 ml of benzene was heated under reflux for 28 hr, allowed to cool, and filtered to remove the precipitated triethylamine hydrobromide. The filtrate was again heated under reflux for 18 hr, allowed to cool, washed with water and saturated sodium chloride solution, dried over anhydrous magnesium sulfate and concentrated to dryness in vacuo. Chromatography over 200 g of silica gel with first ethyl acetate and then with 10% methanol in ethyl acetate afforded 4.4 g of the desired product, Rf(silica—10% methanol/ethyl acetate)=0.3. Recrystallization from 2-propanol gave 3.8 g (62%), mp 99°-100°.

B.

N-[6-[4-(3,4-Dichlorophenyl)-1-piperazinyl]hexyl]-6-methoxy-4-methyl-8-quinolinamine A cold (−40°) slurry of 0.9 g (0.007 mole) of anhydrous aluminum chloride in 20 ml of dry tetrahydrofuran was added to a cold (−30°) slurry of 0.75 g (0.02 mole) of lithium aluminum hydride in 30 ml of tetrahydrofuran. To the stirred mixture, which had been allowed to warm up to −20°, was added dropwise a solution of 2.7 g (0.0052 mole) of 4-(3,4-dichlorophenyl)-N-(6-methoxy-4-methyl-8-quinolinyl)-1-piperazinehexanamide in 30 ml of tetrahydrofuran. The mixture was stirred at −20° −0° for 3 hr, and then treated with 3.3 ml of 30% sodium hydroxide and enough water to clarify the supernatant. The supernatant was decanted from the soft white precipitate which was then washed with additional tetrahydrofuran. The decanted solvent and wash were combined, concentrated in vacuo to remove the tetrahydrofuran, and then combined with water and ether. The ether was washed, dried and concentrated to dryness in vacuo to afford 2.3 g of white solid. Recrystallization from 2-propanol afforded 2.1 g (81%) of the title compound, mp 92°-94°.

EXAMPLE 16

6-Methoxy-4-methyl-N-[6-[4-(2-pyridinyl)-1-piperazinyl]hexyl]-8-quinolimamine

A.

N-(6-Methoxy-4-methyl-8-quinolinyl)-6-[4-(2-pyridinyl)-1-piperazinyl]-hexanamide A mixture of 3.3 g (0.009 mole) of 6-bromo-N-(6-methoxy-4-methyl-8-quinolinyl)hexanamide and 1.8 g (0.01 mole) of 1-(2-pyridinyl)piperazine in 10 ml of toluene was heated in an oil bath at 120° for 2.5 hr. After 1.5 hr, excess triethylamine was added slowly with stirring. After cooling, the reaction mixture was taken up in dichloromethane, washed with water, dried over anhydrous magnesium sulfate, and concentrated to dryness in vacuo. Recrystallization from 2-propanol afforded 3.4 g (85%) of the desired product, mp 120°-121°.

B.

6-Methoxy-4-methyl-N-[6-[4-(2-pyridinyl)-1-piperazinyl]hexyl]-8-quinolinamine

A cold (−40°) slurry of 1.7 g (0.0127 mole) of anhydrous aluminum chloride in 50 ml of tetrahydrofuran was added to an equally cold suspension of 1.35 g (0.0355 mole) of lithium aluminum hydride in 30 ml of tetrahydrofuran. The mixture was stirred and allowed to warm to −10°. A solution of 3.3 g (0.0073 mole) of N-(6-methoxy-4-methyl-8-quinolinyl)-6-[4-(2-pyridinyl)-1-piperazinyl]hexanamide, 0.2 hydrate in 100 ml of tetrahydrofuran was added to the mixture dropwise, with stirring. The mixture was stirred for 3 hr, treated with 6.5 ml of 30% sodium hydroxide solution and with enough water to clarify the supernatant, and filtered through Supercel. The filtrate was concentrated in vacuo to remove most of the tetrahydrofuran, diluted with dichloromethane, washed with water, dried and concentrated to dryness. Recrystallization of the residue from 2-propanol afforded 2.1 g (66%) of the title compound, mp 78°-81°.

EXAMPLE 17

4-(2-Ethyl-1-oxobutyl)-N-(6-methoxy-4-methyl-8-quinolinyl)-1-piperazinehexanamine,dihydrochloride The trihydrobromide salt of 6-methoxy-4-methyl-N-[6-(1-piperazinyl)hexyl]-8-quinolinamine(14.1 g) (Example 1) was converted to the free base. The crude base was dissolved in acetone and to an aliquot calculated to contain 3.2 g (0.009 mole) was added 2.3 g (0.022 mole) of sodium carbonate. Acetone was added to bring the volume to 90 ml and to this mixture was added dropwise, with stirring, a solution of 1.21 g (0.009 mole) of 2-ethylbutyryl chloride in 50 ml of acetone. The mixture was stirred under reflux for 1.5 hr, allowed to cool, filtered, and concentrated under vacuum. The concentrate was diluted with dichloromethane, washed with very dilute ammonium hydroxide and then with water, dried over anhydrous magnesium sulfate and evaporated to dryness under vacuum. The residue was chromatographed over 200 g of silica gel with a 2% solution of methanol in ethyl acetate to afford 2 g of an oil, Rf(silica—10% methanol in ethyl acetate)=0.29. A solution of the oil in 2-propanol was treated with 1.7 ml of a 12% solution of hydrogen chloride in 2-propanol and chilled. The resulting precipitate was collected and dried under vacuum at 50° to afford 1.6 g (33.4%) of the title compound. NMR spectroscopy demonstrated the presence of 0.1 mole of 2-propanol.

EXAMPLE 18

4-[6-[(6-Methoxy-4-methyl-8-quinolinyl)amino]hexyl]-1-piperazinecarboxylic acid, ethyl ester A mixture of 6.0 g (0.0195 mole) of N-(6-chlorohexyl)-6-methoxy-4-methyl-8-quinolinamine and 6 ml of 1-piperazinecarboxylic acid, ethyl ester in 2 ml of toluene was heated in an oil bath at 135° for 3 hr, allowed to cool, diluted with ethyl acetate and toluene, washed with water, dried, and concentrated to dryness in vacuo. The residue was chromatographed over 700 g of silica gel first with 2 l of ethyl acetate and then with 2 l each of the following solutions of methanol in ethyl acetate: 2%, 5%, 10%, and 20%. The eluant containing product, Rf(silica—ethyl acetate)=0.16, was concentrated to dryness. The residue was taken up in ether, filtered to remove dark flocculent material, and then treated with 1.2 ml of 85% phosphoric acid in 30 ml of ethanol. The gum which settled was washed with ether and acetone and then dissolved in 2-propanol and water. The pH of the solution was adjusted to 8 with ammonium hydroxide. The solution was then heated on the steambath, diluted with water to the cloud point and chilled to afford 1.7 g (21%) of the title compound, mp. 59°–60°.

EXAMPLE 19

4-[6-[(6-Methoxy-4-methyl-8-quinolinyl)amino]-hexyl]-1-piperazinecarboxylic acid, phenylmethyl-ester, dihydrochloride

A. 1-Piperazinecarboxylic acid, phenylmethyl ester

A mixture of 17.2 g (0.2 mole) of anhydrous piperazine, 40 ml of water and 60 ml (0.36 mole) of 6N hydrochloric acid in 300 ml of methanol was heated to boiling. Small portions of benzylchloroformate (total 48 g, 0.28 mole) and 4N sodium hydroxide (total 100 ml) were added alternately to maintain a pH of 4.5–5.5. The mixture was heated under reflux for 3 hr, allowed to cool overnight, concentrated in vacuo to remove the methanol, made alkaline with sodium hydroxide and extracted with dichloromethane. The dichloromethane extract was washed with water and then extracted with 400 ml of 1N hydrochloric acid. The acid extract was washed with dichloromethane, made alkaline with sodium hydroxide, and extracted with dichloromethane. The dichloromethane extract was washed with water, dried over anhydrous magnesium sulfate, filtered, and concentrated to dryness in vacuo to give 25 g of crude product. Distillation under vacuum afforded 21.3 g (48%) of the product, bp 140°–143° (0.1 torr). VPC indicated the material consisted of 97% of a single component and the NMR was consistent with the assigned structure.

B.

4-[6-[(6-Methoxy-4-methyl-8-quinolinyl)amino]hexyl]-1-piperazine-carboxylic acid, phenylmethyl ester, dihydrochloride, hydrate (5:2)

A mixture of 6.1 g (0.02 mole) of N-(6-chlorohexyl)-6-methoxy-4-methyl-8-quinolinamine and 4.8 g (0.022 mole) of 1-piperazinecarboxylic acid, phenylmethyl ester was heated at 130° for 2 hr. During the second hour, 2 ml of triethylamine was added portionwise. The mixture was then heated at 150° for 1 hr, allowed to cool, and dissolved in dichloromethane. The solution was washed with water, dried over anhydrous magnesium sulfate, filtered and concentrated to dryness in vacuo. The residue was chromatographed over 230 g of silica gel first with 1 liter of dichloromethane, then with 1 liter of a 1% solution of methanol in dichloromethane, and finally with 3 l of a 3% solution of methanol in dichloromethane. Fractions containing the product, Rf(silica—ethyl acetate)=0.27, were combined and concentrated to dryness in vacuo. The residue was dissolved in 2-propanol and heated with 15 ml of a 12% solution of hydrogen chloride in 2-propanol. The solution was chilled overnight to afford 7.7 g (67%) of the title compound, mp 143°–150° with prior softening.

EXAMPLE 20

N,N-Diethyl-4-[6-[(6-methoxy-4-methyl-8-quinolinyl)-amino]hexyl]-1-piperazinecarboxamide, dihydrochloride

A.

N-(6-Methoxy-4-methyl-8-quinolinyl)-1-piperazinehexanamide

A mixture of 8 g (0.022 mole) of 6-bromo-N-(6-methoxy-4-methyl-8-quinolinyl)-hexanamide and 35 g (0.41 mole) of piperazine was stirred at 125° for 1 hr, cooled and suspended in water. The resulting fine precipitate was collected and dissolved in dichloromethane. The solution was washed with water, dried, and concentrated to dryness in vacuo. The residue was chromatographed over 560 g of alumina with 500 ml each of the following solutions of methanol in an ethyl acetate:dichloromethane (1:9) mixture: 2%, 3%, 4%, 5% and 10% to afford 2.6 g of crude product, Rf(alumina—75 parts of ethyl acetate:25 parts of methanol:1 part of triethylamine)=0.38. Recrystallization from toluene afforded 1.9 g (23%) of the title compound, mp 122°–124°.

B.

6-Methoxy-4-methyl-N-[6-(1-piperazinyl)hexyl]-8-quinolinamine

A cold (−40°) slurry of 3.8 g (0.0285 mole) of anhydrous aluminum chloride in 60 ml of tetrahydrofuran was added to an equally cold suspension of 3.2 g (0.087 mole) of lithium aluminum chloride in 40 ml of tetrahydrofuran. The mixture was allowed to warm to −20° and to it was added portionwise a suspension of 7.8 g (0.021 mole) of N-(6-methoxy-4-methyl-8-quinolinyl)-1-piperazinehexanamide in 300 ml of tetrahydrofuran. The mixture was allowed to stir overnight as it warmed to room temperature, and then was treated with 13.5 ml of 30% sodium hydroxide solution, and with enough water to clarify the supernatant. The supernatant was separated from the sticky precipiate, concentrated in vacuo to remove most of the tetrahydrofuran, diluted with dichloromethane, washed with water, dried and concentrated to dryness in vacuo. The residue was chromatographed over 200 g of silica gel first with 1 liter of ethyl acetate and then with the following solutions of methanol in ethyl acetate: 5% (1 liter), 10% (1 liter), 15% (1 liter), 20% (1 liter) and 25% (4 liters). The eluant containing product, Rf(silica—75 parts ethyl acetate:25 parts of methanol:1 part triethylamine)=0.05, was concentrated to dryness in vacuo to afford 4.4 g (59%) of the desired product of sufficient purity to use in the next step.

C.

N,N-diethyl-4-[6-[(6-methoxy-4-methyl-8-quinolinyl)amino]hexyl]-1-piperazinecarboxamide, dihydrochloride To a mixture of 2.4 g (0.00673 mole) of 6-methoxy-4-methyl-N-[6-(1-piperazinyl)hexyl]-8-quinolinamine and 1.7 g (0.016 mole) of sodium carbonate in 50 ml of acetone was added a solution of 1.8 g (0.007 mole) of diethylcarbamoylchloride in 20 ml of acetone. The mixture was stirred under gentle reflux for 2 hr, allowed to cool, filtered and concentrated to dryness in vacuo. A solution of the residue in dichloromethane was washed with water, dried over anhydrous magnesium sulfate, filtered and concentrated to dryness. Chromatography of the residue over 70 g of silica with 10% methanol in ethyl acetate afforded 2 g of product, Rf=0.3. The material was triturated with 2-propanol containing excess hydrogen chloride. The resulting yellow precipitate was collected, washed with 2-propanol and then ether, dried in vacuo at 52° overnight and air-equilibrated to afford 1.8 g (50%) of the title compound, mp 226°–228° (dec).

EXAMPLE 21

4[6-(6-Methoxy-4-methyl-8-quinolinyl)amino]hexyl]-N,N-diphenyl-1-piperazine-carboxamide, phosphate The trihydrobromide salt of 6-methoxy-4-methyl-N-[6-(1-piperazinyl)hexyl]-8-quinolinamine (14.1 g) (Example 1) was converted to free base. The crude base was dissolved in acetone and to an aliquot calculated to contain 2.6 g (0.0073 mole) was added 1.8 g (0.017 mole) of sodium carbonate. Acetone was added to bring this volume up to 150 ml and to this mixture was added dropwise, with stirring, a solution of 1.7 g (0.0073 mole) of diphenylcarbamylchloride in 50 ml of acetone. The mixture was stirred under reflux for 2 hours, allowed to cool, filtered, and concentrated to dryness under vacuum. A solution of the residue in dichloromethane was washed first with a very dilute solution of ammonium hydroxide and then with water, dried over anhydrous magnesium sulfate, and concentrated. Chromatography of the concentrate over 150 g of silica gel with a 5% solution of methanol in ethyl acetate afforded 3.1 g of crude product, $R_f$(silica—1:25:74 mixture of triethylamine:methanol:ethyl acetate)=0.7, as an oil. A solution of the oil in ether was treated with a solution of 0.9 ml of 85% phosphoric acid in 5 ml of ethanol to afford a gum which was triturated with acetone and 2-propanol. The resulting yellow solid was collected, dried under vacuum first in a desiccator over calcium carbonate and then in an oven at 50° to afford 2.7 g (45%) of the title compound, mp 90°–100°. NMR spectroscopy confirms the presence of approximately 0.2 mole of 2-propanol.

EXAMPLE 22

N-Cyano-4-[6-[(6-methoxy-4-methyl-8-quinolinyl)amino]hexyl]-1-piperazinecarboximidothioic acid, methyl ester A. 1-Piperazinecarboxylic acid, phenylethyl ester To a stirred mixture of 20.7 g (0.24 mole) of anhydrous piperazine in 20 ml of water and 200 ml of acetic acid was added dropwise 30 ml (0.2 mole) of benzylchloroformate. The temperature rose from 22° to 30°. The mixture was stirred overnight, diluted with 10 ml of concentrated hydrochloric acid and extracted with dichloromethane. The aqueous layer was chilled with ice, made alkaline with 50% sodium hydroxide solution and extracted with dichloromethane. The extract was washed with water, dried over anhydrous magnesium sulfate and concentrated to dryness under vacuum to afford 30 g (68%) of the desired compound. Vpc indicated that the material was 97.6% homogenous and the nmr spectrum was consistent with the assigned structure.

B.

4-[6-[(6-Methoxy-4-methyl-8-quinolinyl)amino]-hexyl]-1-piperazine carboxylic acid, phenylmethyl ester A mixture of 15.35 g (0.05 mole) of N-(6-chlorohexyl)-6-methoxy-4-methyl-8-quinolinamine and 12.1 g (0.055 mole) of 1-piperazinecarboxylic acid, phenyl-methyl ester was heated at 148°–150° for 4 hours. After 2 hours of heating, 10 ml of triethylamine was slowly added. The reaction mixture was allowed to cool, diluted with dichloromethane, washed first with dilute ammonium hydroxide and then with water, dried and concentrated under vacuum. The concentrate was chromatographed over 500 g of silica gel first with dichloromethane, then with a 1% polution of methanol in dichloromethane and finally with a 2% solution of methanol in dichloromethane to afford 20 g of crude product, $R_f$(silica—ethyl acetate)=0.27. Trituration with a 10:1 mixture of cyclohexane:2-propanol afforded 18.6 g (75.6%) of the desired product, mp 73°–73.5°.

C.

6-Methoxy-4-methyl-N-[6-(1-piperazinyl)hexyl]-8-quinolinamine, trihydrobromide

A mixture of 0.55 g (0.0011 mole) of 4-[6-[(6-methoxy-4-methyl-8-quinolinyl)amino]hexyl]-1-piperazinecarboxylic acid, phenylmethyl ester and 0.5 ml of 45% hydrobromic acid in 4 ml of acetic acid was heated on a steambath for 2 hours, allowed to cool and diluted with ether. The resulting gum was triturated with additional ether and then with 2-propanol. The gold precipitate which formed, was collected, washed with 2-propanol and ether, dried under vacuum at 75° and allowed to equilibrate in air to afford 0.6 g (87%) of the desired compound, mp 240°–242° (dec). The nmr spectrum confirmed the presence of about 0.3 mole of 2-propanol.

D.

N-Cyano-4-[6-[(6-methoxy-4-methyl-8-quinolinyl)amino]hexyl]-1-piperazinecarboximidothioic acid, methyl ester A solution of 5.5 g (0.009 mole) of 6-methoxy-4-methyl-N-[6-(1-piperazinyl)hexyl]-8-quinolinamine, trihydrobromide, compd. with 2-propanol (1:0.3), hemihydrate in 100 ml of water was made basic with concentrated ammonium hydroxide and extracted with dichloromethane. The extract was washed, dried over anhydrous magnesium sulfate, filtered, and concentrated to dryness under vacuum. A solution of the concentrate and 1.8 g (0.012 mole) of cyanodithioimidocarbonic acid, dimethyl ester in 100 ml of toluene was stirred at room temperature for 64 hours, then washed with water, dried, and concentrated to dryness. Recrystallization from 2-propanol afforded 2.7 g (66%) of the title compound as yellow needles, mp 97°–99°.

EXAMPLE 23

4-(Ethylsulfonyl)-N-(6-methoxy-4-methyl-8-quinolinyl)-1-piperazinehexanamine

A.

N-(6-Chlorohexyl)-6-methoxy-4-methyl-8-quinolinamine

To a stirred solution of 7.8 g (0.027 mole) of 6-[(6-methoxy-4-methyl-8-quinolinyl)amino-1-hexanol in 90 ml of dichloromethane at 5° was added dropwise a solution of 1.9 ml (0.03 mole) of thionylchloride in 25 ml of dichloromethane. The mixture was allowed to warm to room temperature overnight, poured into iced water, and made basic with concentrated ammonium hydroxide. The resulting emulsion was filtered and the layers then separated. The organic portion was washed, dried, and concentrated to afford 7.9 g (96%) of crude product which was used in the next step without further purification. TLC(silica—thyl acetate) indicated that the product, Rf=0.65, was slightly contaminated with the starting hexanol, Rf=0.4.

B. 4-(Ethylsulfonyl)-N-(6-methoxy-4-methyl-8-quinolinyl)-1-piperazinehexan-amine A mixture of 1.5 g. (0.0049 mole) of N-(6-chlorohexyl)-6-methoxy-4-methyl-8-quinolinamine and 2.7 g (0.015 mole) of 1-(ethylsulfonyl)-piperazine was heated at 130° for 50 min, allowed to cool and taken up in dichloromethane and water. The organic layer was washed again, dried, and concentrated to dryness in vacuo. The residue was chromatographed over 70 g of silica gel first with ethyl acetate and then with 2% methanol in ethyl acetate. The eluant containing product, Rf(silica—ethyl acetate)=0.05, was concentrated to dryness in vacuo. Recrystallization of the residue from 2-propanol afforded 1.5 g (68%) of the title compound, mp 72°-74°.

EXAMPLE 24

N-[6-(Hexahydro-4-methyl-1H-1,4-diazepin-1-yl)hexyl]-6-methoxy-4-methyl-8-quinolinamine

A. Hexahydro-N-(6-methoxy-4-methyl-8-quinolinyl)-4-methyl-1H-1,4-diazepine-1-hexanamide A mixture of 6.7 g (0.0183 mole) of 6-bromo-(6-methoxy-4-methyl-8-quinolinyl)hexanamide and 3.4 g (0.03 mole) of hexahydro-1-methyl-1H-1,4-diazepine in 100 ml of toluene was stirred at 100° for 20 hr, allowed to cool and combined with water and additional toluene. The toluene layer was separated from the aqueous layer and thick black oil which had formed, washed with water, dried, and concentrated in vacuo. Recrystallization of the residue from hexane afforded 2.7 g (40%) of the desired product, mp 74°-77°. Chilling the filtrate afforded an additional 0.6 g. Total yield: 3.3 g (45%).

B. N-[6-(Hexahydro-4-methyl-1H-1,4-diazepin-1-yl)hexyl]-6-methoxy-4-methyl-8-quinolinamine, (Z)-2-butenedioate(1:2.4)

To 30 ml of tetrahydrofuran at −50° was added 1.5 g (0.011 mole) of anhydrous aluminum chloride. The slurry was added to a slurry of 1.25 g (0.033 mole) of lithium aluminum hydride in 75 ml of tetrahydrofuran at −30° and the mixture was stirred and allowed to warm to −20°. To the mixture was added dropwise a solution of 3.3 g (0.0083 mole) of hexahydro-N-(6-methoxy-4-methyl-8-quinolinyl)-4-methyl-1H-1,4-diazepine-1-hexanamide in 100 ml of tetrahydrofuran, keeping the temperature of the mixture at −20° to −10°. The reaction mixture was allowed to warm to room temperature overnight. 5.3 ml of 30% sodium hydroxide and enough water were added to give a clear supernatant. The mixture was filtered and concentrated. The conentrate was combined with ether and water; the ether layer was separated, washed with more water, dried, and concentrated. The residue was triturated with a solution of hydrogen chloride in 2-propanol (approximately 10%). The resulting solid, which became a gum upon standing, was dissolved in water and the solution was made basic and extracted with ether. The ether extract was washed, dried, concentrated and chromatographed over a 30 g column of silica gel with 20% methanol and 1% triethylamine in ethylacetate, to afford 1.6 g of an oil. The oil was dissolved in 2-propanol and combined with a solution of 1 g (0.0086 mole) of (Z)-2-butenedioic acid in 20 ml of methanol. The resulting yellow solid was collected, washed with 2-propanol and ether, immediately placed in a desiccator under vacuum for 4 hr and then dried at 70° in vacuo for 66 hr. The chunky solid was crushed and redried to afford 2.5 g (45%) of the title compound, mp 137°-139°. The nmr confirms the presence of 2.4 mole of (Z)-2-butenedioic acid.

EXAMPLE 25

N-[6-(2,6-Dimethyl-4-morpholinyl)hexyl]-6-methoxy-4-methyl-8-quinolinamine

A. N-(6-Methoxy-4-methyl-8-quinolinyl)-2,6-dimethyl-4-morpholinehexanamide

A mixture of 5.5 g (0.015 mole) of 6-bromo-N-(6-methoxy-4-methyl-8-quinolinyl)hexanamide and 1.85 ml (0.018 mole) of 2,6-dimethylmorpholine in 90 ml of benzene was heated under reflux for 24 hr. Triethylamine (2 ml) was added and the mixture was heated under reflux for an additional 2 hr, allowed to cool, and filtered. The filtrate was washed with water, dried and concentrated. TLC(silica gel—ethyl acetate) demonstrated a mixture of the unchanged bromo compound, Rf(silica—ethyl acetate)=0.63, and the product, Rf=0.08. A solution of the residue, 1.3 ml (0.01 mole) of 2,6-dimethylmorpholine, and 1.5 ml of triethylamine in 80 ml of benzene was heated under reflux for 40 hr, allowed to cool, filtered, washed with water, dried and concentrated. The residue was chromatographed over 200 g of silica gel with 1 liter each of the following solutions of methanol in ethyl acetate: 1.5%, 2%, 3% to afford 3.7 g of crude product. Recrystallization from hexane afforded 3.3 g of the title compound, mp 87°-90°. The NMR spectrum confirmed the presence of hexane.

B. N-[6-(2,6-Dimethyl-4-morpholinyl)hexyl]-6-methoxy-4-methyl-8-quinolinamine, dihydrochloride A cold (−40°) slurry of 1.1 g (0.008 mole) of anhydrous aluminum chloride in 50 ml of tetrahydrofuran was added to a cold (−40°) suspension of 0.9 g (0.024 mole) of lithium aluminum hydride in 25 ml of tetrahydrofuran and the stirred mixture was allowed to warm to −20°. To it was added dropwise a solution of 2.1 g (0.005 mole) of N-(6-methoxy-4-methyl-8-quinolinyl)-2,6-dimethyl-4-morpholine-hexanamide, compd with hexane(1:0.2) in 100 ml of tetrahydrofuran. The mixture was stirred for 3 hr allowing it to warm to 15°. To it were added 3.8 ml of 30% sodium hydroxide solution and enough water to cause the coagulation of inorganic material. The supernatant was decanted and concentrated in vacuo to remove most of the tetrahydrofuran and then taken up in dichloromethane and water. The dichloromethane was separated, washed again, dried and concentrated. Recrystallization of the residue from 2-propanol containing hydrogen chloride afforded the product as the dihydrochloride salt. The yellow-orange material was collected, washed with cold 2-propanol and ether, dried in vacuo at 81° for 4 hr and allowed to air-equilibrate to give 1.3 g (53%), mp 223°-226° (dec). The NMR spectrum confirmed the presence of 0.3 mole of 2-propanol.

EXAMPLE 26

6-Methoxy-4-methyl-N-[6-(4-thiamorpholinyl)hexyl]-8-quinolinamine,dihydrochloride

N-(6-Methoxy-4-methyl-8-quinolinyl)-4-thiamorpholinehexanamide

A mixture of 6.5 g (0.0163 mole) of 6-bromo-(6-methoxy-4-methyl-8-quinolinyl)-hexanamide, 1.9 g (0.018 mole) of thiomorpholine and 1.8 g (0.0130 mole) of triethylamine in 100 ml of benzene was heated under reflux for 37 hr. Additional thiomorpholine (2 g) and triethyl amine (2 g) were added after 12 hr and after 30 hr of heating. The cool reaction mixture was filtered and concentrated to dryness in vacuo. Recrystallization of the residue from 2-propanol afforded 5.6 g (89%) of the desired product, mp 89°–91°.

6-Methoxy-4-methyl-N-[6-(4-thiamorpholinyl)hexyl]-8-quinolinamine,dihydrochloride To 50 ml of tetrahydrofuran at −50° was added 2.7 g (0.02 mole) of anhydrous aluminum chloride. The slurry was added to a mixture of 2.2 g (0.058 mole) of lithium aluminum hydride in 100 ml of tetrahydrofuran at −30° and the mixture was stirred and allowed to warm to −20°. A solution of 5.6 g (0.0144 mole) of N-(6-methoxy-4-methyl-8-quinolinyl)-4-thiamorpholine-hexanamide in 50 ml of tetrahydrofuran was added to the mixture dropwise. The mixture was stirred at −10° for 3 hr, allowed to warm to room temperature and treated with 9.2 ml of 30% sodium hydroxide and 150 ml of water. The mixture was filtered through celite and concentrated to dryness in vacuo. The residual oil was chromatographed over 200 g of silica gel first with ethyl acetate and then with 2% methanol in ethyl acetate. The eluant containing product, Rf(silica gel—ethyl acetate)=0.17, was concentrated and the residual oil was taken up in 2-propanol and treated with excess of a saturated solution of hydrogen chloride in 2-propanol. The resulting precipitate was collected, washed with 2-propanol and dried in vacuo at 60° to afford 5.4 g (82%) of the title compound, mp 257°–259° (dec). The presence of 2-propanol was confirmed by NMR spectroscopy.

EXAMPLE 27

6-Methoxy-4-methyl-N-[6-(4-thiamorpholinyl)hexyl]-8-quinolinamine,S-oxide

A mixture of 1.5 g (0.0033 mole) of 6-methoxy-4-methyl-N-[6-(4-thiamorpholinyl)hexyl]-8-quinolinamine (Example 26) compound with 2-propanol(1:0.2), dihydrochloride, and 5 ml of 30% hydrogen peroxide in 50 ml of acetic acid and 5 ml of water was stirred overnight, combined with ice, made basic with 50% sodium hydroxide, and extracted with chloroform. The chloroform extract was washed, dried over anhydrous magnesium sulfate and concentrated to dryness in vacuo. The residue was triturated with a solution of hydrogen chloride (ca. 5%) in 2-propanol to afford 0.6 g, mp 253°–256° (dec). The same procedure was repeated with an additional 1.6 g (0.0035 mole) of the starting material, the same amounts of acetic acid and water and 2 ml of 30% hydrogen peroxide to afford 0.8 g, mp 254°–256° (dec). The two lots were combined and dried in vacuo at 80° for 3 hr to afford 1.4 g (43%) of the title compound, mp 252°–255° (dec). The IR spectrum of the material exhibited absorption (1030 cm$^{-1}$) characteristic of sulfoxide.

EXAMPLE 28

6-Methoxy-4-methyl-N-[6-(4-thiamorpholinyl)-hexyl]-8-quinolinamine-S,S-dioxide

6-Methoxy-4-methyl-N-[6-(4-thiamorpholinyl)hexyl]-8-quinolinamine,S,S-dioxide A mixture of 3.1 g (0.01 mole) of N-(6-chlorohexyl)-6-methoxy-4-methyl-8-quinolinamine and 1.4 g (0.01 mole) of thiamorpholine, dioxide in 5 ml of toluene was stirred in an oil bath at 120° for 3 hr, during which time 1.5 ml of triethylamine was added intermittently. The mixture was heated in an oil bath at 140° for 3 hr. An additional 1 g of thiamorpholine dioxide was added and the mixture was stirred in an oil bath at 150° for an additional 1.5 hr. After cooling, the mixture was taken up in dichloromethane, washed with water, dried over anhydrous magnesium sulfate and concentrated in vacuo to dryness. The residue was chromatographed over 200 g of silica with ethyl acetate to afford 3.7 g of crude product, Rf(silica—ethyl acetate)=0.3. Recrystallization from 2-propanol gave 2.9 g (71.6%) of the title compound, mp 92°–94°.

EXAMPLE 29

Trans-N-(6-methoxy-4-methyl-8-quinolinyl)-2,6-dimethyl-4-thiamorpholinehexanamide and cis-N-(6-methoxy-4-methyl-8-quinolinyl)-2,6-dimethyl-4-thiamorpholinehexanamide A mixture of 6 g (0.0164 mole) of 6-bromo-(6-methoxy-4-methyl-8-quinolinyl)hexanamide and 4.3 g (0.0328 mole) of a mixture of cis and trans-2,6-dimethylthiamorpholines in 100 ml of benzene was heated under reflux for 11 hr. An additional 1 g of the thiamorpholine was added after 5 hr of heating and a further 3 g after 7 hr. Approximately 4 g of triethylamine was added to the cooled mixture and the resulting precipitate was removed by filtration. The filtrate was combined with 2 g of the thiamorpholine, heated under reflux for 4 hr, allowed to cool, washed with water, dried (anhydrous magnesium sulfate) and concentrated to dryness in vacuo. TLC(silica—ethyl acetate) demonstrated the presence of the bromo starting material (Rf=0.71) as well as two major products, the trans isomer (Rf=0.5) and the cis isomer (Rf=0.25). The mixture was chromatographed over 250 g of silica gel with ethyl acetate to afford 3.2 g of a mixture of the trans isomer and starting material, 0.7 g of clean trans isomer and 1.8 g of the cis. The mixture of the trans isomer and starting material was rechromatographed over 100 g of silica gel with a 4:6 mixture of ethyl acetate and toluene to give an additional 2.2 g of the trans isomer. Small samples of each isomer were recrystallized from n-hexane to give analytical material; trans, mp 61°–63°, and cis, mp 75°–77°.

The original assignment of isomers was reversed, based on a more rigorous spectral analysis, which revealed coupling constant differences between the cis and trans isomers. These differences are a result of predictable conformational differences. A similar analysis of the cis and trans isomers of the analogous 2,6-dimethylmorpholine, has been described by Booth and Gidley (H. Booth and G. C. Gidley, Tetrahedron, 21, 3429 (1965). It is assumed that the cis isomer exists primarily in the conformation in which the bulky methyl groups are equatorial as shown in Formula 1. The trans isomer, in which one methyl group is equatorial and the other axial, should exist in an equilibrium situation as shown in Formula 2. The predicted coupling constants for these conformations are based on prior art as discussed by Bible (R. B. Bible, "Interpretation of NMR Spectra", Plenum Press, New York, 1965, pp 35-36).

It has been determined that the cis isomer is approximately 3 to 4 times more effective than the trans isomer when SD$_{90}$ values (1.51:0.43) are compared.

The description of the subject invention includes detailed reference to specific embodiments to ensure a thorough understanding of the making and using thereof. It is to be understood, however, that these specific embodiments are considered merely exemplary of those within the scope of the invention defined by the claims which follow.

Formula 1

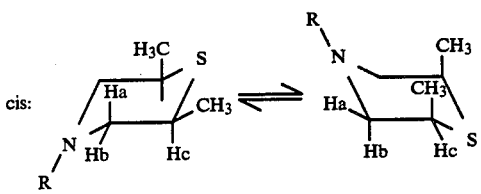

Formula 2

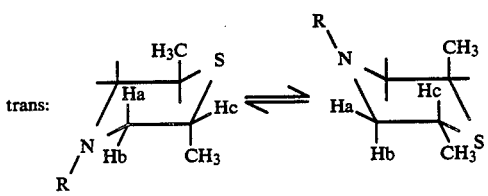

We claim:

1. A lepidine compound having the formula:

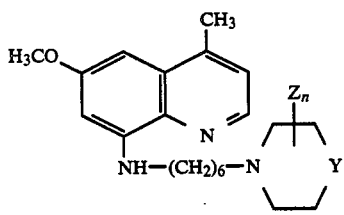

wherein

Z represents methyl and n is an integer from 0 to 2;

Y represents —O—, —S—, —S(O)—, —S(O)$_2$—, and —N(R')—;

R' represents hydrogen, lower alkyl, mono- or di-R" substituted lower alkyl, sulfonyl, saturated 1,4-diazepinyl, lower alkyl N-cyanocarboximidothioate, —C(O)R''', phenyl, pyridyl, naphthyl, or mono or disubstituted phenyl wherein the substituent is lower alkyl, lower alkoxy, phenyl-lower alkoxy, amino, lower alkylamino, hydrogen or halogen;

R" represents hydroxy, lower alkoxy, phenyl-lower alkoxy, amino, lower alkyl substituted amino, phenyl, halogenated phenyl, or sulfonyl; and R''' represents lower alkyl, lower alkoxy, phenyl-lower alkoxy, amino, lower alkyl substituted amino; and a pharmaceutically acceptable salt thereof.

2. The compound of claim 1 wherein Y is —O—.

3. The compound of claim 1 wherein the lepidine derivative is N-[6-(2,6-dimethyl-4-morpholinyl)hexyl]-6-methoxy-4-methyl-8-quinolinamine.

4. The compound of claim 1 wherein Y is —S—.

5. The compound of claim 4 wherein the lepidine derivative is 6-methoxy-4-methyl-N-[6-(4-thiamorpholinyl)hexyl]-8-quinolinamine.

6. The compound of claim 4 wherein the lepidine derivative is trans-N-(6-methoxy-4-methyl-8-quinolinyl)-2,6-dimethyl-4-thiamorpholinehexanamide.

7. The compound of claim 4 wherein the lepidine derivative is cis-N-(6-methoxy-4-methyl-8-quinolinyl)-2,6-dimethyl-4-thiamorpholine hexanamide.

8. The compound of claim 1 wherein Y is —S(O)—.

9. The compound of claim 8 wherein the lepidine derivative is 6-methoxy-4-methyl-N-[6-(4-thiamorpholinyl)hexyl]-8-quinolinamine,S-oxide.

10. The compound of claim 1 wherein Y is —S(O)$_2$—.

11. The compound of claim 10 wherein the lepidine derivative is 6-Methoxy-4-methyl-N-[6-(4-thiamorpholinyl)-hexyl]-8-quinolinamine-S,S-dioxide.

12. The compound of claim 1 wherein Y is —N(R')—.

13. The compound of claim 12 wherein R' is hydrogen.

14. The compound of claim 13 wherein the lepidine is 6-methoxy-4-methyl-N-[6-(1-piperazinyl)hexyl]-8-quinolinamine.

15. The compound of claim 13 wherein the lepidine is N-[6-(3,5-dimethyl-1-piperazinyl)hexyl]-6-methoxy-4-methyl-8-quinolinamine.

16. The compound of claim 12 wherein R' is a lower alkyl.

17. The compound of claim 16 wherein the lepidine is 6-methoxy-4-methyl-N-[6-(4-methyl-1-piperazinyl)-hexyl]-8-quinolinamine.

18. The compound of claim 16 wherein the lepidine is 6-methoxy-4-methyl-N-[6-(2-methyl-4-(3-methylbutyl-1-piperazinyl]-hexyl-8-quinolinamine.

19. The compound of claim 10 wherein R' is a mono- or di-R" substituted lower alkyl.

20. The compound of claim 19 wherein R" is hydroxy.

21. The compound of claim 20 wherein the lepidine is 4-[6-[(6-methoxy-4-methyl-8-quinolinyl)amino]-hexyl]-1-piperazinepropanol.

22. The compound of claim 20 wherein the lepidine is 4-[6-[(6-methoxy-4-methyl-8-quinolinyl)amino]-hexyl]-alpha-methyl-1-piperazine-ethanol.

23. The compound of claim 20 wherein the lepidine is 3-[4-[6[[6-methoxy-4-methyl-8-quinolinyl]amino]hexyl]-1-piperazinyl]-1,2-propanediol.

24. The compound of claim 19 wherein R" is alkyl sulfonyl.

25. The compound of claim 24 wherein the lepidine is N-[6-[4-[2-(ethylsulfonyl)ethyl]-1-piperazinyl]-hexyl]-6-methoxy-4-methyl-8-quinolinamine.

26. The compound of claim 19 wherein R" is phenyl-lower alkoxy.

27. The compound of claim 26 wherein the lepidine is N-[6-[4-[2-(diphenylmethoxy)ethyl]-1-piperazinyl]-hexyl]-6-methoxy-4-methy-1-8-quinolinamine.

28. The compound of claim 19 wherein R" is lower alkyl substituted amino.

29. The compound of claim 28 wherein the lepidine is N-[6-[4-[3-(dimethylamino)propyl]-1-piperazinyl]-hexyl]-6-methoxy-4-methyl-8-quinolinamine.

30. The compound of claim 19 wherein R" is one each of hydroxy and lower alkyl substituted amino.

31. The compound of claim 30 wherein the lepidine is alpha[(diethylamino)methyl]-4-[6-[(6-methoxy-4-methyl-8-quinolinyl)amino]hexyl]-1-piperazineethanol.

32. The compound of claim 19 wherein R" is one of each of pheny and halogenated phenyl.

33. The compound of claim 32 wherein the lepidine is N-[6-[4-[(4-chlorophenyl)phenylmethyl]-1-piperazinyl]-hexyl]-6-methoxy-4-methyl-8-quinolinamine.

34. The compound of claim 12 wherein R' is substituted phenyl.

35. The compound of claim 34 wherein the lepidine is N-[6-[4-(3,4 dichlorophenyl)-1-piperazinyl]hexyl]-6-methoxy-4-methyl-8-quinolinamine.

36. The compound of claim 12 wherein the lepidine is 6-methoxy-4-methyl-N-[6-[4-(2-pyridinyl)-1-piperazinyl]hexyl]-8-quinolinamine.

37. The compound of claim 12 wherein R' is —C(O)R'''.

38. The compound of claim 37 whrein R''' is lower alkyl.

39. The compound of claim 38 wherein the lepidine is 4-(2-ethyl-1-oxobutyl)-N-(6-methoxy-4-methyl-8-quinolinyl)-1-piperazinehexanamine.

40. The compound of claim 37 wherein R''' is lower alkoxy.

41. The compound of claim 40 wherein the lepidine is ethyl 4-[6-[(6-methoxy-4-methyl-8-quinolinyl)amino]-hexyl]-1-piperazinecarboxylate.

42. The compound of claim 37 wherein R''' is phenyl-lower alkoxy.

43. The compound of claim 42 wherein the lepidine is benzyl 4-[6-[(6-methoxy-4-methyl-8-quinolinyl)amino]-hexyl]-1-piperazinecarboxylate.

44. The compound of claim 37 wherein R''' is lower alkyl substituted amino.

45. The compound of claim 44 wherein the lepidine is N,N-diethyl-4-[6-[(6-methoxy-4-methyl-8-quinolinyl)-amino]hexyl]-1-piperazine-carboxamide.

46. The compound of claim 12 wherein R' is lower alkyl N-cyanocarboximidothioate.

47. The compound of claim 46 wherein the lepidine is methyl N-cyano-4-[6-[(6-methoxy-4-methyl-8-quinolinyl-)amino]hexyl]-1-piperazine-carboximidothioate.

48. The compound of claim 12 wherein R' is sulfonyl.

49. The compound of claim 12 wherein the lepidine is 4-(ethylsulfonyl)-N-(6-methoxy-4-methyl-8-quinolinyl)-1-piperazinehexanamine.

50. The compound of claim 53 wherein R' is saturated 1,4-diazepinyl.

51. The compound of claim 53 wherein the lepidine is N-[6-(hexahydro-4-methyl-1H-1,4-diazepin-1-yl)hexyl]-6-methoxy-4-methyl-8-quinolinamine.

52. A lepidine compound having the formula:

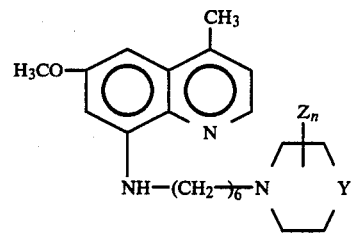

wherein Z represents methyl and N is an integer from 0 to 2; y represents —O—, —S— or N(R'); R' represents H, lower alkyl, mono or di R" substituted lower alkyl, saturated 1,4-diazepinyl, lower alkyl N-cyanocarboximidothioate, C(O)R''', phenyl, pyridyl, mono or disubstituted phenyl wherein the substituent is halogen; R" represents phenyl-lower alkoxy, amino, hydroxy, lower alkoxy, lower alkyl substituted amino, phenyl, halogenated phenyl and; and R''' represents lower alkyl, phenyl lower alkoxy, amino, lower alkyl substituted amino; and a pharmaceutically acceptable salt thereof.

53. A lepidine compound of claim 52 wherein Z is CH₃, and Y is selected from the group consisting essentially of —O—, —S—,

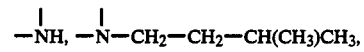

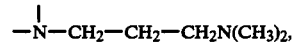

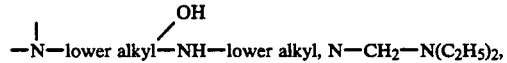

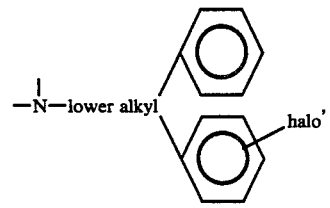

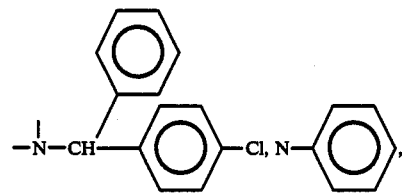

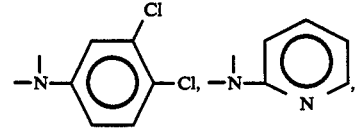

-continued

—N|—C(O)—CH$_2$CH(C$_2$H$_5$)CH$_2$CH$_3$,

—N—C(O)O lower alkyl phenyl, —N|—C(O)OCH$_2$—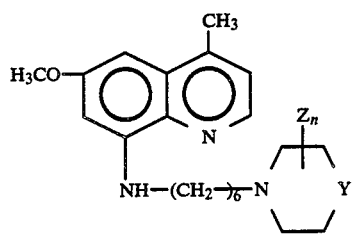,

—N|—C(O)NH—lower alkyl, —N|—C(O)N(C$_2$H$_5$)$_2$,

—N|—(lower alkyl)—N—cyanocarboximidothioate,

—N|(methyl) N—cyanocarboximidothioate,

—N—N⟨N—H⟩ and —N—N⟨N—CH$_3$⟩.

54. A method for the treatment of leishmaniasis which comprises administering parenterally or orally to an animal a leishmanicidally effective amount of a lepidine derivative having the formula:

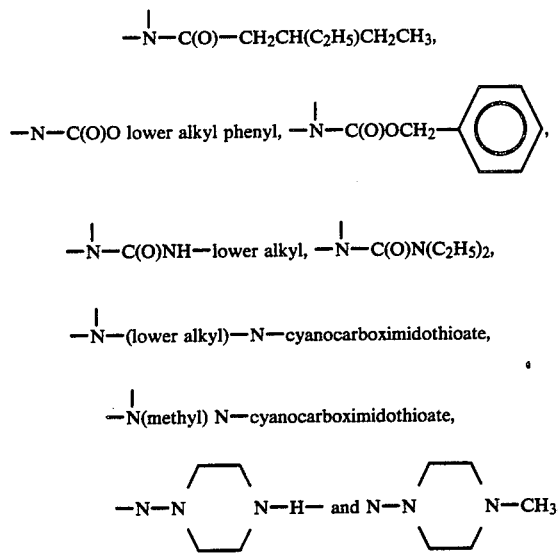

wherein Z represents methyl and n is an integer from 0 to 2; y represents —O—, —S— or N(R'); R' represents H, lower alkyl, mono or di R" substituted lower alkyl, saturated 1,4-diazepinyl, lower alkyl N-cyanocarboximidothioate, C(O)R''', phenyl, pyridyl, mono or disubstituted phenyl wherein the substituent is halogen; R" represents phenyl-lower alkoxy, amino, hydroxy, lower alkoxy, lower alkyl substituted amino, phenyl, halogenated phenyl R''' represents lower alkyl, phenyl lower alkoxy, amino, lower alkyl substituted amino; and a pharmaceutically acceptable salt thereof.

55. The method of claim 54 wherein Z is CH$_3$, and Y is selected from the group consisting essentially of —O—, —S—,

—N|H, —N|—CH$_2$—CH$_2$—CH(CH$_3$)CH$_3$,

N|—lower alkylene oxyalkaryl,

—N|—CH$_2$—CH(OCH$_2$—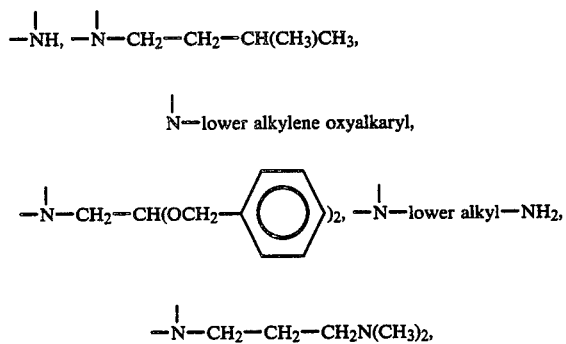

—N|—CH$_2$—CH$_2$—CH$_2$N(CH$_3$)$_2$.

-continued

—N|—lower alkyl—NH—lower alkyl, N—CH$_2$N(C$_2$H$_5$)$_2$—,

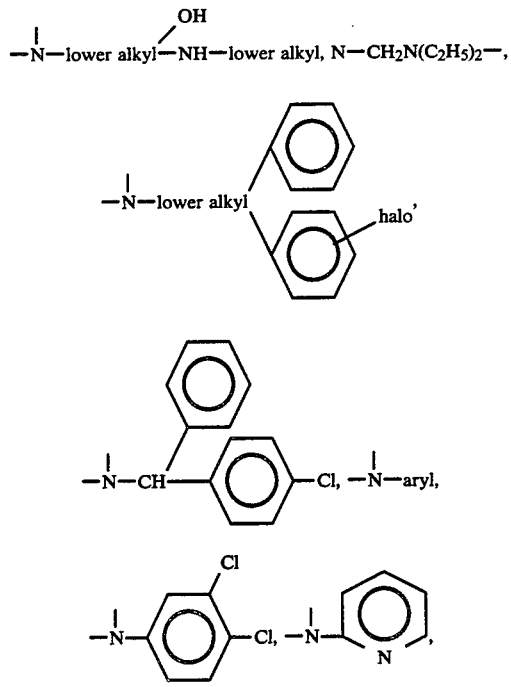

—N|—C(O)—CH$_2$CH(C$_2$H$_5$)CH$_2$CH$_3$,

—N|—C(O)Oalkaryl, —N|—C(O)OCH$_2$—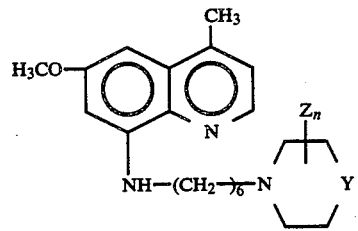,

—N|—C(O)NH—lower alkyl, —N|—C(O)N(C$_2$H$_5$)$_2$,

—N|—(lower alkyl)—N—cyanocarboximidothioate,

—N|(methyl) N—cyanocarboximidothioate,

—N—N⟨N—H⟩ and —N—N⟨N—CH$_3$⟩.

56. A method for the treatment of leishmaniasis which comprises administering parenterally or orally to an animal a leishmanicidally effective amount of a lepidine derivative having the formula:

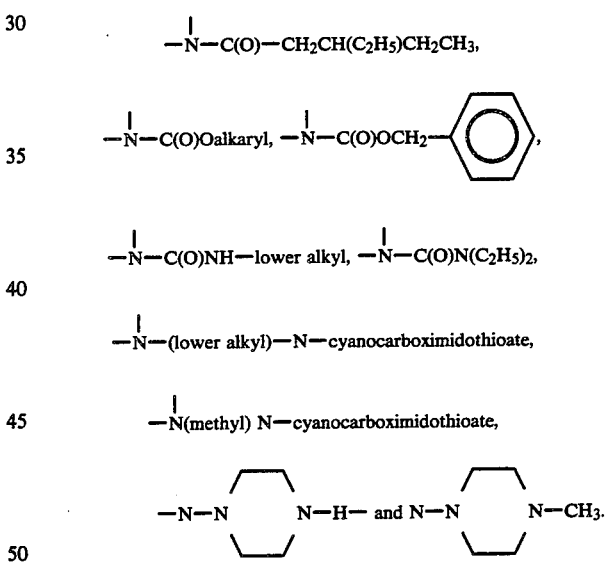

wherein
Z represents methyl and n is an integer form 0 to 2;

Y represents —O—, —S—, —S(O)—, —s(O)$_2$—, and —N(R$^1$)—;

R' represents hydrogen, lower alkyl, mono or di R" substituted lower alkyl, sulfonyl, saturated 1,4-diazepinyl, lower alkyl N-cyanocarboximidothioate, —C(O)''', phenyl, pyridyl, naphthyl, or mono or disubstituted phenyl wherein the substituent is lower alkyl, lower alkoxy, phenyl-lower alkoxy, amino, lower alkylamino, hydrogen or halogen;

R" represents hydroxy, lower alkoxy, phenyl-lower alkoxy, amino, lower alkyl substituted amino, phenyl, halogenated phenyl, or sulfonyl; and R''' represents lower alkyl, lower alkoxy, phenyl-lower alkoxy, amino, lower alkyl substituted amino; and a pharmaceutically acceptable salt thereof.

* * * * *